(12) United States Patent
Cao et al.

(10) Patent No.: US 8,899,977 B2
(45) Date of Patent: Dec. 2, 2014

(54) ORTHODONTIC REPOSITIONING APPLIANCES HAVING IMPROVED GEOMETRY, METHODS AND SYSTEMS

(75) Inventors: Heng Cao, Santa Clara, CA (US); Vadim Matov, San Jose, CA (US); John Y. Morton, San Jose, CA (US); Jon Moss, Antioch, CA (US); Ryan Kimura, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 515 days.

(21) Appl. No.: 12/324,714

(22) Filed: Nov. 26, 2008

(65) Prior Publication Data

US 2009/0191502 A1    Jul. 30, 2009

Related U.S. Application Data

(60) Provisional application No. 61/024,536, filed on Jan. 29, 2008.

(51) Int. Cl.
*A61C 3/00* (2006.01)
*A61C 7/08* (2006.01)

(52) U.S. Cl.
CPC .................................. *A61C 7/08* (2013.01)
USPC .................................................. 433/24

(58) Field of Classification Search
USPC ............... 433/2, 5–7, 18–19, 24, 219
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen | |
| 3,860,803 A | 1/1975 | Levine | |
| 3,916,526 A | 11/1975 | Schudy | |

(Continued)

FOREIGN PATENT DOCUMENTS

| | | |
|---|---|---|
| AU | 3031677 | 5/1979 |
| AU | 517102 | 7/1981 |

(Continued)

OTHER PUBLICATIONS

Alcaniz, et al., "An Advanced System for the Simulation and Planning of Orthodontic Treatments," Karl Heinz Hohne and Ron Kikinis (eds.), *Visualization in Biomedical Computing, 4th Int'l. Conf., VBC '96*, Hamburg, Germany, Sep. 22-25, 1996, Springer-Verlag, pp. 511-520.

(Continued)

*Primary Examiner* — Yogesh Patel
(74) *Attorney, Agent, or Firm* — Wilson Sonsini Goodrich & Rosati

(57) ABSTRACT

The present invention provides methods and systems including orthodontic tooth positioning appliances. An exemplary appliance can include teeth receiving cavities shaped such that, when worn by a patient, repositioning the patient's teeth from a first arrangement toward a subsequent or target arrangement. Appliances can include a cavity having one or more shaped features or protrusions shaped and/or positioned so as to apply a desired force to a patient's tooth received in the cavity and move the tooth along a desired path or direction.

22 Claims, 28 Drawing Sheets

(56) References Cited

U.S. PATENT DOCUMENTS

| | | |
|---|---|---|
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,077,647 B2 | 7/2006 | Choi et al. |
| 7,156,661 B2 | 1/2007 | Choi et al. |
| 7,374,421 B2 * | 5/2008 | Solomon .................. 433/18 |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2004/0229183 A1 * | 11/2004 | Knopp et al. .................. 433/6 |
| 2005/0048433 A1 | 3/2005 | Hilliard |

(56) References Cited

U.S. PATENT DOCUMENTS

| | | | |
|---|---|---|---|
| 2005/0055118 | A1 | 3/2005 | Nikolskiy et al. |
| 2005/0106525 | A1* | 5/2005 | Knopp et al. .................. 433/6 |
| 2006/0188834 | A1* | 8/2006 | Hilliard ........................ 433/24 |
| 2006/0223022 | A1* | 10/2006 | Solomon ........................ 433/6 |

FOREIGN PATENT DOCUMENTS

| | | |
|---|---|---|
| AU | 5598894 | 6/1994 |
| CA | 1121955 | 4/1982 |
| DE | 2749802 | 5/1978 |
| DE | 69327661 | 7/2000 |
| EP | 0091876 | 10/1983 |
| EP | 0299490 | 1/1989 |
| EP | 0376873 | 7/1990 |
| EP | 0490848 | 6/1992 |
| EP | 0541500 | 5/1993 |
| EP | 0667753 | 8/1995 |
| EP | 0731673 | 9/1996 |
| EP | 0774933 | 5/1997 |
| ES | 463897 | 1/1980 |
| FR | 2369828 | 6/1978 |
| FR | 2652256 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 | 8/1990 |
| WO | WO 91/04713 | 4/1991 |
| WO | WO 94/10935 | 5/1994 |
| WO | WO 98/32394 | 7/1998 |
| WO | WO 98/44865 | 10/1998 |
| WO | WO 98/58596 | 12/1998 |

OTHER PUBLICATIONS

"Important Tip About Wearing the Red White & Blue Active Clear Retainer System," Allesee Orthodontic Appliances—Pro Lab, 1 page (No Date Given).
"Inside the ADA," JADA, 118:286-294 (Mar. 1989).
"The Choice Is Clear: Red, White & Blue . . . The Simple, Affordable, No-Braces Treatment," Allesee Orthodontic Appliances—Pro Lab product information for doctors, <http://ormco.com/aoa/appliancesservice/RWB/doctor.html>, 5 pages (May 19, 2003).
"The Choice is Clear: Red, White & Blue . . . The Simple, Affordable, No-Braces Treatment," Allesee Orthodontic Appliances—Pro Lab product information for patients, <http://ormco.com/aoa/appliancesservice/RWB/patients.html>, 2 pages (May 19, 2003).
"The Choice Is Clear: Red, White & Blue . . . The Simple, Affordable, No-Braces Treatment," Allesee Orthodontic Appilances—Pro Lab product information, 6 pages (2003).
"The Red, White & Blue Way to Improve Your Smile!" Allesee Orthodontic Appliances—Pro Lab product information for patients, 2 pages (No Date Given).
"You May Be a Candidate for This Invisible No-Braces Treatment," Allesee Orthodontic Appliances—Pro Lab product information for patients, 2 pages (No Date Given).
Alexander et al., "The DigiGraph Work Station Part 2 Clinical Management," JCO, pp. 402-407 (Jul. 1990).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).

Altschuler, "3D Mapping of Maxillo-Facial Prosthesis," AADR Abstract #607, 2 pages total, (1980).
American Association for Dental Research, Summary of Activities, Mar. 20-23, 1980, Los Angeles, CA, p. 195.
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (No Date Given).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive, Tonawanda, New York. 14150-5890, 20 pages total (No Date Given).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/~pbourke/projection/coords>.
Boyd et al., "Three Dimensional Diagnosis and Orthodontic Treatment of Complex Malocclusions With the Invisalign Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstracts, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).

(56) References Cited

OTHER PUBLICATIONS

Chafetz et al., "Subsidence of the Femoral Prosthesis, A Stereophotogrammetric Evaluation," *Clin. Orthop. Relat. Res.*, No. 201, pp. 60-67 (Dec. 1985).
Chiappone, (1980). Constructing the Gnathologic Setup and Positioner, *J. Clin. Orthod*, vol. 14, pp. 121-133.
Cottingham, (1969). Gnathologic Clear Plastic Positioner, *Am. J. Orthod*, vol. 55, pp. 23-31.
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, *Canadian Dental Journal*, vol. 54(9), pp. 661-666 (1988).
Crawford, "CAD/CAM in the Dental Office: Does It Work?", *Canadian Dental Journal*, vol. 57, No. 2, pp. 121-123 (Feb. 1991).
Crooks, "CAD/CAM Comes to USC," *USC Dentistry*, pp. 14-17 (Spring 1990).
Cureton, Correcting Malaligned Mandibular Incisors with Removable Retainers, *J. Clin. Orthod*, vol. 30, No. 7 (1996) pp. 390-395.
Curry et al., "Integrated Three-Dimensional Craniofacial Mapping at the Craniofacial Research Instrumentation Laboratory/University of the Pacific," *Semin. Orthod.*, 7(4):258-265 (Dec. 2001).
Cutting et al., "Three-Dimensional Computer-Assisted Design of Craniofacial Surgical Procedures: Optimization and Interaction with Cephalometric and CT-Based Models," *Plast. Reconstr. Surg.*, 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for "Gingiva," Dictionary.com, pp. 1-3, retrieved from the Internet on Nov. 5, 2004, URL <http://reference.com/search/search?q=gingiva>.
DeFranco et al., "Three-Dimensional Large Displacement Analysis of Orthodontic Appliances," *J. Biomechanics*, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (No Date Given).
DENT-X posted on Sep. 24, 1998 at <http://www.dent-x.com/DentSim.htm>, 6 pages.
Doyle, "Digital Dentistry," *Computer Graphics World*, pp. 50-52, 54 (Oct. 2000).
DuraClear™ product information, Allesee Orthodontic Appliances—Pro Lab, 1 page (No Date Given).
Duret et al, "CAD-CAM in Dentistry," *J. Am. Dent. Assoc.*, 117:715-720 (Nov. 1988).
Duret et al., "CAD/CAM Imaging in Dentistry," *Curr. Opin. Dent.*, 1:150-154 (1991).
Duret, "The Dental CAD/CAM, General Description of the Project," *Hennson International Product Brochure*, 18 pages total, Jan. 1986.
Duret,"Vers Une Prosthese Informatisee," (English translation attached), *Tonus*, vol. 75, pp. 55-57 (Nov. 15, 1985).
Economides, "The Microcomputer in the Orthodontic Office," *JCO*, pp. 767-772 (Nov. 1979).
Elsasser, Some Observations on the History and Uses of the Kesling Positioner, *Am. J. Orthod.* (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," *Am. J. Orthod.*, 73(1):36-46 (Jan. 1978).
Felton et al., "A Computerized Analysis of the Shape and Stability of Mandibular Arch Form," *Am. J. Orthod. Dentofacial Orthop.*, 92(6):478-483 (Dec. 1987).
Friede et al., "Accuracy of Cephalometric Prediction in Orthognathic Surgery," Abstract of Papers, *J. Dent. Res.*, 70:754-760 (1987).
Fütterling et al., "Automated Finite Element Modeling of a Human Mandible with Dental Implants," WSCG '98—Conference Program, retrieved from the Internet: <http://wscg.zcu.cz/wscg98/papers98/Strasser_98.pdf>, 8 pages.

Gao et al., "3-D element Generation for Multi-Connected Complex Dental and Mandibular Structure," Proc. Int'l Workshop on Medical Imaging and Augmented Reality, pp. 267-271 (Jun. 12, 2001).
Gim-Alldent Deutschland, "Das DUX System: Die Technik," 2 pages total (No Date Given).
Gottleib et al., "JCO Interviews Dr. James A. McNamura, Jr., on the Frankel Appliance: Part 2: Clinical Management," *J. Clin. Orthod.*, 16(6):390-407 (Jun. 1982).
Grayson, "New Methods for Three Dimensional Analysis of Craniofacial Deformity, Symposium: Computerized Facial Imaging in Oral and Maxiiofacial Surgery," *AAOMS*, 3 pages total, (Sep. 13, 1990).
Guess et al., "Computer Treatment Estimates in Orthodontics and Orthognathic Surgery," *JCO*, pp. 262-228 (Apr. 1989).
Heaven et al., "Computer-Based Image Analysis of Artificial Root Surface Caries," Abstracts of Papers, *J. Dent. Res.*, 70:528 (Apr. 17-21, 1991).
Highbeam Research, "Simulating Stress Put on Jaw," Tooling & Production [online], Nov. 1996, pp. 1-2, retrieved from the Internet on Nov. 5, 2004, URL <http://static.highbeam.com/t/toolingamp-production/november011996/simulatingstressputonia . . . >.
Hikage, "Integrated Orthodontic Management System for Virtual Three-Dimensional Computer Graphic Simulation and Optical Video Image Database for Diagnosis and Treatment Planning", *Journal of Japan Orthodontic Society*, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), *Informatbnen*, pp. 375-396 (Mar. 1991).
Hojjatie et al., "Three-Dimensional Finite Element Analysis of Glass-Ceramic Dental Crowns," *J. Biomech.*, 23(11):1157-1166 (1990).
Huckins, "CAD-CAM Generated Mandibular Model Prototype from MRI Data," *AAOMS*, p. 96 (1999).
"JCO Interviews, Craig Andreiko, DDS, MS on the Elan and Orthos Systems," *JCO*, pp. 459-468 (Aug. 1994).
"JCO Interviews, Dr. Homer W. Phillips on Computers in Orthodontic Practice, Part 2," *JCO*, pp. 819-831 (Dec. 1983).
Jerrold, "The Problem, Electronic Data Transmission and the Law," *AJO-DO*, pp. 478-479 (Apr. 1988).
Jones et al., "An Assessment of the Fit of a Parabolic Curve to Pre- and Post-Treatment Dental Arches," *Br. J. Orthod.*, 16:85-93 (1989).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case Reports, J. Nihon University School of Dentistry (1982) 24(1):1-27.
Kanazawa et al., "Three-Dimensional Measurements of the Occlusal Surfaces of Upper Molars in a Dutch Population," *J. Dent Res.*, 63(11):1298-1301 (Nov. 1984).
Kochanek, "Interpolating Splines with Local Tension, Continuity and Bias Control," *Computer Graphics*, 18(3):33-41 (Jul. 1984).
Kesling et al., The Philosophy of the Tooth Positioning Appliance, *American Journal of Orthodontics and Oral Surgery* (1945) 31:297-304.
Kesling, Coordinating the Predetermined Pattern and Tooth Positioner with Conventional Treatment, *Am. J. Orthod. Oral Surg.* (1946) 32:285-293.
Kleeman et al., The Speed Positioner, *J. Clin. Orthod.* (1996) 30:673-680.
Kunii et al., "Articulation Simulation for an Intelligent Dental Care System," *Displays* 15:181-188 (1994).
Kuroda et al., Three-Dimensional Dental Cast Analyzing System Using Laser Scanning, *Am. J. Orthod. Dentofac. Orthop.* (1996) 110:365-369.
Laurendeau, et al., "A Computer-Vision Technique for the Acquisition and Processing of 3-D Profiles of Dental Imprints: An Application in Orthodontics," *IEEE Transactions on Medical Imaging*, 10(3):453-461 (Sep. 1991).
Leinfelder, et al., "A New Method for Generating Ceramic Restorations: a CAD-CAM System," *J. Am. Dent. Assoc.*, 118(6):703-707 (Jun. 1989).

(56) References Cited

OTHER PUBLICATIONS

Manetti, et al., "Computer-Aided Cefalometry and New Mechanics in Orthodontics," (Article Summary in English, article in German), *Fortschr. Kieferorthop.* 44, 370-376 (Nr. 5), 1983.
McCann, "Inside the ADA," *J. Amer. Dent. Assoc.*, 118:286-294 (Mar. 1989).
McNamara et al., "Invisible Retainers," *J. Clin. Orthod.*, pp. 570-578 (Aug. 1985).
McNamara et al., *Orthodontic and Orthopedic Treatment in the Mixed Dentition*, Needham Press, pp. 347-353 (Jan. 1993).
Moermann et al., "Computer Machined Adhesive Porcelain Inlays: Margin Adaptation after Fatigue Stress," IADR Abstract 339, *J. Dent. Res.*, 66(a):763 (1987).
Moles, "Correcting Mild Malalignments—As Easy as One, Two, Three," *AOA/Pro Corner*, vol. 11, No. 1, 2 pages (2002).
Mörmann et al., "Marginale Adaptation von adhäsuven Porzellaninlays in vitro," Separatdruck aus: Schweiz. Mschr. Zahnmed. 95: 1118-1129, 1985.
Nahoum, "The Vacuum Formed Dental Contour Appliance," *N. Y. State Dent. J.*, 30(9):385-390 (Nov. 1964).
Nash, "CEREC CAD/CAM Inlays: Aesthetics and Durability in a Single Appointment," *Dent. Today*, 9(8):20, 22-23 (Oct. 1990).
Nishiyama et al., "A New Construction of Tooth Repositioner by LTV Vinyl Silicone Rubber," *J. Nihon Univ. Sch. Dent.*, 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," *Dentist*, 3 pages total, Jan./Feb. 1989.
Pinkham, "Inventor's CAD/CAM May Transform Dentistry," *Dentist*, 3 pages total, Sep. 1990.
Ponitz, "Invisible Retainers," *Am. J. Orthod.*, 59(3):266-272 (Mar. 1971).
PROCERA Research Projects, "PROCERA Research Projects 1993—Abstract Collection," pp. 3-28 (1993).
Proffit et al., *Contemporary Orthodontics*, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <httpz;//www.essix.com/magazine/default.html> Aug. 13, 1997, 7 pages.
Redmond et al., "Clinical Implications of Digital Orthodontics," *Am. J. Orthod. Dentofacial Orthop.*, 117(2):240-242 (2000).
Rekow et al., "CAD/CAM for Dental Restorations—Some of the Curious Challenges," *IEEE Trans. Biomed. Eng.*, 38(4):344-345 (Apr. 1991).
Rekow et al., "Comparison of Three Data Acquisition Techniques for 3-D Tooth Surface Mapping," *Annual International Conference of the IEEE Engineering in Medicine and Biology Society*, 13(1):344-345 (1991).
Rekow, "A Review of the Developments in Dental CAD/CAM Systems," (contains references to Japanese efforts and content of the papers of particular interest to the clinician are indicated with a one-line summary of their content in the bibliography), *Curr. Opin. Dent.*, 2:25-33 (Jun. 1992).
Rekow, "CAD/CAM in Dentistry: A Historical Perspective and View of the Future," *J. Can. Dent. Assoc.*, 58(4):283, 287-288 (Apr. 1992).
Rekow, "Computer-Aided Design and Manufacturing in Dentistry: A Review of the State of the Art," *J. Prosthet. Dent.*, 58(4):512-516 (Oct. 1987).
Rekow, "Dental CAD-CAM Systems: What is the State of the Art?", *J. Amer. Dent. Assoc.*, 122:43-48 (1991).
Rekow, "Feasibility of an Automated System for Production of Dental Restorations, Ph.D. Thesis," Univ. of Minnesota, 244 pages total, Nov. 1988.
Richmond et al., "The Development of the PAR Index (Peer Assessment Rating): Reliability and Validity," *Eur. J. Orthod.*, 14:125-139 (1992).

Richmond et al., "The Development of a 3D Cast Analysis System," *Br. J. Orthod.*, 13(1):53-54 (Jan. 1986).
Richmond, "Recording the Dental Cast in Three Dimensions," *Am. J. Orthod. Dentofacial Orthop.*, 92(3)199-206 (Sep. 1987).
Rudge, "Dental Arch Analysis: Arch Form, A Review of the Literature," *Eur. J. Orthod.*, 3(4):279-284.
Sakuda et al., "Integrated Information-Processing System in Clinical Orthodontics: An Approach with Use of a Computer Network System," *Am. J. Orthod. Dentofacial Orthop.*, 101(3): 210-220 (Mar. 1992).
Schellhas et al., "Three-Dimensional Computed Tomography in Maxillofacial Surgical Planning," *Arch. Otolamgol. Head Neck Surg.*, 114:438-442 (Apr. 1988).
Sheridan et al., "Essix Appliances: Minor Tooth Movement with Divots and Windows," *JCO on CD-ROM* 1994:659-663 (1997).
Schroeder et al., Eds. *The Visual Toolkit*, Prentice Hall PTR, New Jersey (1998) Chapters 6, 8 & 9, (pp. 153-210,309-354, and 355-428, respectively).
Shilliday, (1971). Minimizing finishing problems with the minipositioner, *Am. J. Orthod.* 59:596-599.
Siemens, "CEREC—Computer-Reconstruction," High Tech in der Zahnmedizin, 14 pages total (No Date Given).
Sinclair, "The Readers' Corner," *J. Clin. Orthod.*, 26(6):369-372 (Jun. 1992).
Sirona Dental Systems GmbH, *CEREC 3D, Manuel utiiisateur*, Version 2.0X (in French), 2003,114 pages total.
Stoll et al., "Computer-aided Technologies in Dentistry," (article summary in English, article in German), *Dtsch Zahna'rztl Z* 45, pp. 314-322 (1990).
Sturman, "Interactive Keyframe Animation of 3-D Articulated Models," Proceedings Graphics Interface '84, May-Jun. 1984, pp. 35-40.
Truax L., "Truax Clasp-Less(TM) Appliance System," *Funct. Orthod.*, 9(5):22-4, 26-8 (Sep.-Oct. 1992).
Tru-Tain Orthodontic & Dental Supplies, Product Brochure, Rochester, Minnesota 55902, 16 pages total (No Date Given).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," *J. Dent. Res.*, p. 1100 (Jul.-Aug. 1972).
Van Der Linden, "A New Method to Determine Tooth Positions and Dental Arch Dimensions," *J. Dent. Res.*, 51(4):1104 (Jul.-Aug. 1972).
Van Der Zel, "Ceramic-Fused-to-Metal Restorations with a New CAD/CAM System," *Quintessence Int.*, 24(11):769-778 (1993).
Varady et al., "Reverse Engineering of Geometric Models—An Introduction," *Computer-Aided Design*, 29(4):255-268,1997.
Verstreken et al., "An Image-Guided Planning System for Endosseous Oral Implants," *IEEE Trans. Med. Imaging*, 17(5):842-852 (Oct. 1998).
Warunek et al., Physical and Mechanical Properties of Elastomers in Orthodonic Positioners, *Am J. Orthod. Dentofac. Orthop*, vol. 95, No. 5, (May 1989) pp. 399-400.
Warunek et.al., Clinical Use of Silicone Elastomer Applicances, *JCO* (1989) XXIII(10):694-700.
Wells, Application of the Positioner Appliance in Orthodontic Treatment, *Am. J. Orthodont.* (1970) 58:351-366.
Williams, "Dentistry and CAD/CAM: Another French Revolution," *J. Dent. Practice Admin.*, pp. 2-5 (Jan./Mar. 1987).
Williams, "The Switzerland and Minnesota Developments in CAD/CAM," *J. Dent. Practice Admin.*, pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.

(56) References Cited

OTHER PUBLICATIONS

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL <http://wscg.zcu.cz/wscg98/wscg98.h>.

Xia et al., "Three-Dimensional Virtual-Reality Surgical Planning and Soft-Tissue Prediction for Orthognathic Surgery," *IEEE Trans. Inf. Technol. Biomed.*, 5(2):97-107 (Jun. 2001).

Yamamoto et al., "Optical Measurement of Dental Cast Profile and Application to Analysis of Three-Dimensional Tooth Movement in Orthodontics," *Front. Med. Biol. Eng.*, 1(2):119-130 (1988).

Yamamoto et al., "Three-Dimensional Measurement of Dental Cast Profiles and Its Applications to Orthodontics," *Conf. Proc. IEEE Eng. Med. Biol. Soc.*, 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," *Nippon Dental Review*, 452:61-74 (Jun. 1980).

Yoshii, "Research on a New Orthodontic Appliance: The Dynamic Positioner (D.P.); II. The D.P.Manufacturing Procedure and Clinical Applications," *Nippon Dental Review*, 454:107-130 (Aug. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," *Nippon Dental Review*, 458:112-129 (Dec. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," *Nippon Dental Review*, 457:146-164 (Nov. 1980).

Smith and Burstone, "Mechanics of tooth movement," *Am. J. Orthod.* 85: 294-307 (1984).

\* cited by examiner

US 8,899,977 B2

ORTHODONTIC REPOSITIONING APPLIANCES HAVING IMPROVED GEOMETRY, METHODS AND SYSTEMS

CROSS-REFERENCE TO RELATED APPLICATION

The present invention claims the benefit of priority under 35 U.S.C. §119(e) of U.S. Provisional Application No. 61/024,536, filed Jan. 29, 2008, the entire content of which is incorporated herein by reference.

BACKGROUND OF THE INVENTION

The present invention relates generally to the field of orthodontics, and more particularly to dental repositioning appliances having improved or optimized geometries incorporating one or more shaped features or protrusions.

An objective of orthodontics is to move a patient's teeth to positions where function and/or aesthetics are optimized. Traditionally, appliances such as braces are applied to a patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as software technology available from Align Technology, Inc. The design of the aligners can rely on computer modeling of a series of planned successive tooth arrangements, and the individual aligners are designed to be worn over the teeth and elastically reposition the teeth to each of the planned tooth arrangements.

Orthodontic appliances, in general, apply force and torque on a tooth crown to move teeth, with the applied force typically normal with respect to the surface of a tooth or attachment positioned on the tooth. The tooth root and/or other anatomical structures may hinder the desired tooth movement and render the center of resistance down below the gingival line and in the tooth bone socket, which can make certain movements difficult to accomplish by application of force to the tooth crown. If a translational movement is desired, for example, the translational force is optimally applied through the center of resistance or with sufficient counterbalancing forces, otherwise force on the tooth crown by an appliance can cause unwanted torque with respect to the center of resistance. Clinically, the unwanted torque can result in unwanted tooth movement and root movement, thereby decreasing the effectiveness of the treatment. As appliances are designed to contact and apply forces to the crown of the tooth, and the tooth center of resistance lies below the gingival line, applying forces more directly about the center of resistance is difficult with existing appliances. Accordingly, improved appliances and techniques are needed for applying more effective tooth movement forces to the teeth during orthodontic treatment, and reducing unwanted tooth movements.

SUMMARY OF THE INVENTION

The present invention provides improved orthodontic appliances and related methods for more effectively applying tooth moving forces and repositioning teeth into a desired arrangement. Appliances of the invention include repositioning appliances having improved or optimized geometries incorporating one or more shaped features or protrusions.

In one aspect, the present invention provides methods and systems, including an appliance having teeth receiving cavities shaped such that, when worn by a patient, apply a repositioning force to move the patient's teeth from a first arrangement toward a subsequent or target arrangement. Appliances can include a cavity having one or more shaped features or protrusions. Such features or protrusions can be shaped and/or or positioned to apply a desired force to a patient's tooth received in the cavity so as to more effectively move the tooth along a desired path or direction.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

The invention described herein describes systems and methods including orthodontic appliances having geometries designed to provide more precise control of the forces and moments applied to a tooth, thereby providing better control of the type of tooth movement desired while avoiding unwanted movements, such as unwanted tipping. Appliances according to the present invention can be designed to include certain "shaped features", such as shaped protrusions (e.g., ridges, dimples, etc.) positioned in a tooth receiving cavity, incorporated into appliance design and structure.

Figure 1A:
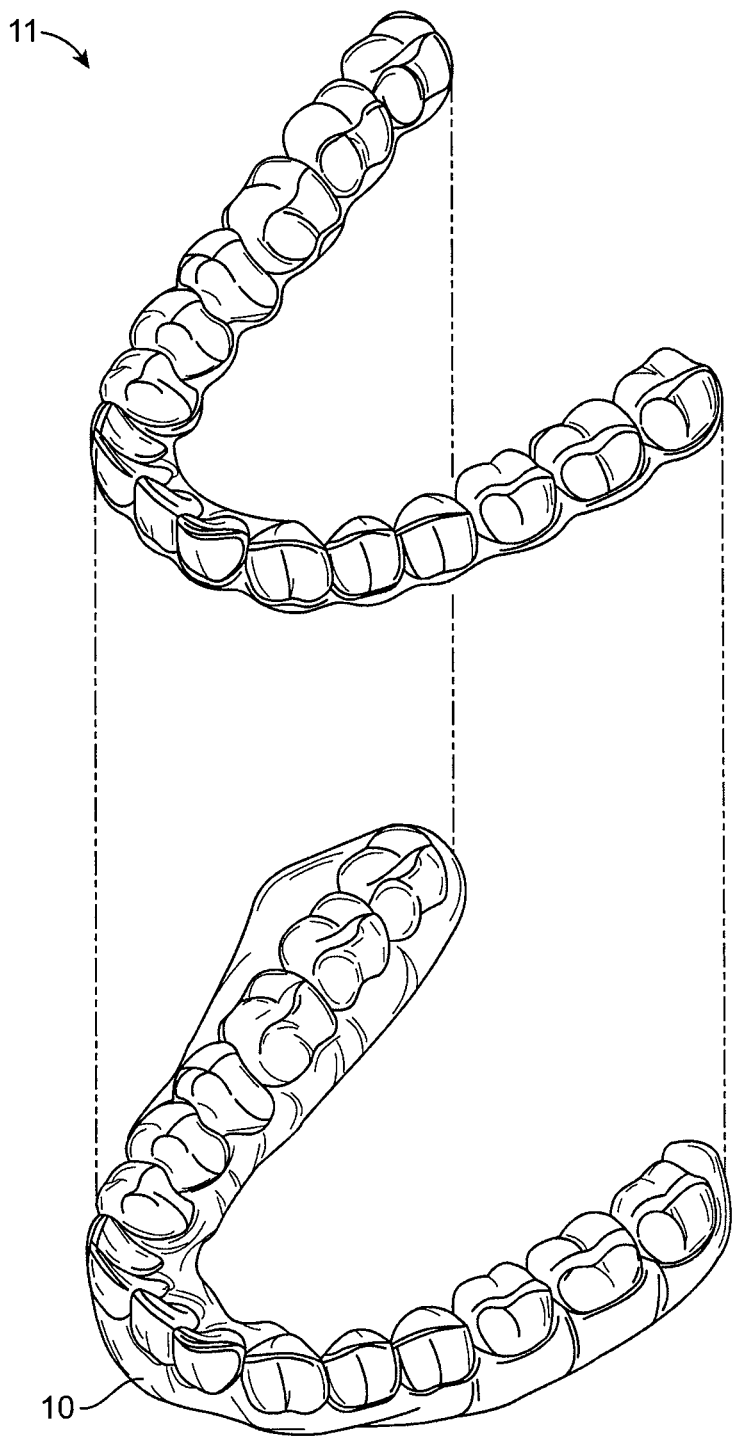
FIG. 1A illustrates a jaw together with an incremental positioning adjustment appliance according to an embodiment of the present invention.

Appliances having teeth receiving cavities that receive and reposition teeth, e.g., via application of force due to appliance resiliency, are generally illustrated with regard to FIG. 1A. As illustrated, FIG. 1A shows one exemplary adjustment appliance 10 which is worn by the patient in order to achieve an incremental repositioning of individual teeth in the jaw 11. The appliance can include a shell (e.g., polymeric shell) having teeth-receiving cavities that receive and resiliently reposition the teeth. Similar appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com"). Appliances according to the present invention further include one or more shaped features disposed in a tooth receiving cavity of the appliance, as further described below. As further described herein, shapes features can be designed, located and distributed to precisely control the moments produced on a patient's tooth as the appliance is worn by the patient. Incorporation of such protrusions and shaped features as described herein can advantageously improve design and effectiveness of appliances and clinical results by more precisely applying force vectors of necessary magnitude and direction for desired movement. Appliances of the present invention having shaped features as described further provide efficient force distribution mechanism that can more effectively reduce unwanted force and moment. Furthermore, inclusion of a force driven method of treatment design that focuses on the causes of tooth movement provides advantages in effectiveness and movement control compared to existing displacement driven treatment designs.

As set forth in the prior applications, an appliance can be designed and/or provided as part of a set or plurality of appliances. In such an embodiment, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt. A plurality of different appliances (e.g., set) can be designed and even fabricated prior to the patient wearing any appliance of the plurality. At that point, the patient replaces the current adjustment appliance with the next adjustment appliance in the series until no more appliances remain. The appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Orthodontic appliances, such as illustrated in FIG. 1A, impart forces to the crown of a tooth at each point of contact between a tooth receiving cavity of the appliance and received tooth. The magnitude of each of these forces and their distribution on the surface of the tooth determines the type of orthodontic tooth movement which results. Types of tooth movement are conventionally delineated as tipping, translation and root movement. Tooth movement of the crown greater than the movement of the root is referred to as tipping. Equivalent movement of the crown and root is referred as translation. Movement of the root greater than the crown is referred to as root movement.

The supporting structures of the tooth offer resistance to movement of the tooth. The multitude of resistances offered by the tissues may be considered all as one, effectively offering resistance centered about a point located within the root of the tooth, termed the center of resistance. A force imparted directly to the center of resistance would result in translation of the tooth. Appliances are often not capable of providing force at the center of resistance. A force imparted to the crown of the tooth can produce a moment about the center of resistance that results in tipping of the tooth. A second force (and/or additional forces) applied to the crown of the tooth can be selected produce a moment to counteract the initial moment. If the moment produced by the second force is equivalent in magnitude an opposite in direction the moments are cancelled and translation of the tooth is accomplished. Increase of the moment produced by the second force beyond balancing the initial moment will result in root movement.

For illustrative purposes, three types of tooth movement can be identified as divisions of a continuum of possible movements. Tooth movements may be in any direction in any plane of space. The present disclosure uses the orthodontic convention of delineating movements in three dimensional space into three classifications: first order, second order and third order.

The magnitudes of the forces selected and applied to the teeth, and the proper selection of the locations and distributions on the tooth surface upon which they act, are important to controlling the type of tooth movement which is achieved. Previously existing appliance technology does not provide for the specific selecting of the location of force application as provided herein, or the calibrated magnitude of force or determination of the moments produced by the forces.

In one aspect, the present invention describes appliances having a design and configuration selected to provide more precise control of relationships of the forces and moments applied to a tooth, hence, better controlling the type of tooth movement achieved and increasing the ability of the aligner to achieve all types of tooth movement (e.g., first order, second order, third order). In particular, the present invention describes incorporation of certain "shaped features" into appliance design and structure. As further described herein, shapes features can be designed, located and distributed to precisely control the moments produced on a patient's teeth as an appliance is worn by the patient. Any number of shaped features can be utilized for improved teeth repositioning as described herein. Embodiments described herein can include features including various shaped protrusions in an appliance cavity (e.g., ridge-like protrusions, dimples, etc.). In one example, a combination of shaped features, such as a combination of attachment-type and non-attachment type (e.g., protrusions) shaped features can be utilized to control the force system produced by an orthodontic appliance.

Shaped features can be incorporated into an appliance design, more particularly, design of teeth receiving cavities of an appliance as illustrated above (see, e.g., FIG. 1A). Shaped features can be designed both in terms of physical/structural features as well as positioning and/or location within a tooth receiving cavity, to distribute appropriate forces in terms of direction and magnitude onto the crown of the received tooth. Thus, the force direction and/or force magnitude can be selected and controlled by positioning the features for contact at different areas or locations on the crown, as well as by the parameters of the feature itself. Exemplary parameters of the shaped feature include but are not limited to cross section shape, prominence, length, width, and radius. Shaped features can be integrated with or added to the existing surfaces of an appliance that is shaped and designed based on (e.g., matching) the position of the patient's teeth at a subsequent arrangement (e.g., n+1 arrangement).

In another embodiment, however, an appliance surface or cavity feature can be further modified to compensate for an effect (e.g., appliance distortion) due to incorporating the shaped feature into the appliance design/use. In one embodiment, for example, appliance modification can include an altered or inflated appliance surface, where the appliance surface is modified so as to remove certain forces coming only from those features of the appliance in contact with the crown other than the shaped features. Modification in this manner provides optimization of use of the shaped features, as well as a precise delivery system for force and moment only necessary for desired tooth movement.

Various designs, orientations, and/or configurations of shaped features are available for use according to the present invention. Shaped features to achieve force profiles favorable to specific types of tooth movement can include both attachment-type features as well as non-attachment type features. Non-attachment type features can include various shaped alterations or protrusions in a surface of an appliance, such as ridges (e.g., interior or exterior), dimples, and the like. The terms "non-attachment type feature" and "protrusion" (e.g., appliance protrusion) are typically used interchangeably herein. Dimples include protrusions having substantially the same dimensions along a width compared to the protrusion length. Ridges, by comparison, include protrusions having unequal length and width. Interior protrusions, such as interior ridges, include a groove or protrusion in an appliance that recesses toward an inner surface (e.g., tooth contacting surface) of the appliance, whereas exterior protrusions and ridges bulge toward an exterior surface of the appliance. Protrusion type features, such as dimples and ridges can be either filled with material (e.g., composite material) or left unfilled. If it is filled, the composite can be controlled to solidify after desired shape and/or volume of the filler is obtained. In the following discussion, the general term feature will be used. But the methods apply on any feature as appropriate.

In some instances, ridge-shaped protrusions may provide differences and/or advantages for force application compared to other protrusion shapes, such as dimples. For example, dimples having substantially equal length compared to with will typically provide more of a point application of a force to a surface of a tooth. By comparison, a ridge-shaped protrusion may allow application force application more evenly distributed along a surface of a tooth, and may provide more precisely controlled tooth movement in some instances. Further, ridge-shaped protrusions by providing more protrusion configuration and design options, provide a greater range of force values that can be selected and delivered to the target tooth compared to non-ridge shapes, such as dimples, and can therefore be more likely to impart the desired load. As such, use of ridges compared to other more simplified shapes (e.g., a single dimple) provide a greater range of available force values or selections for imparting the desired load vector, or force direction and/or magnitude along a tooth surface, thereby providing more treatment options.

Figure 1B:
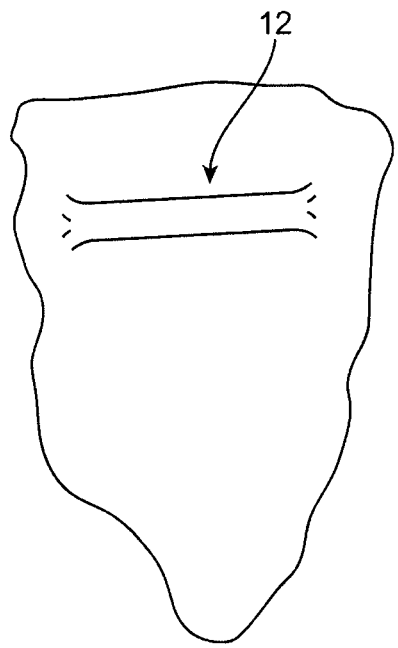
FIGS. 1B-1E illustrate various protrusion configurations and orientations including horizontal continuous ridge (FIG. 1B), vertical continuous ridge (FIG. 1C), and discontinuous ridge (FIGS. 1D and 1E), according to several embodiments of the present invention.
Figure 1C:
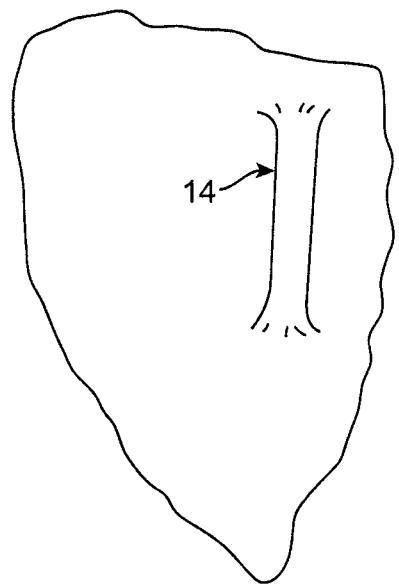
Figure 1D:
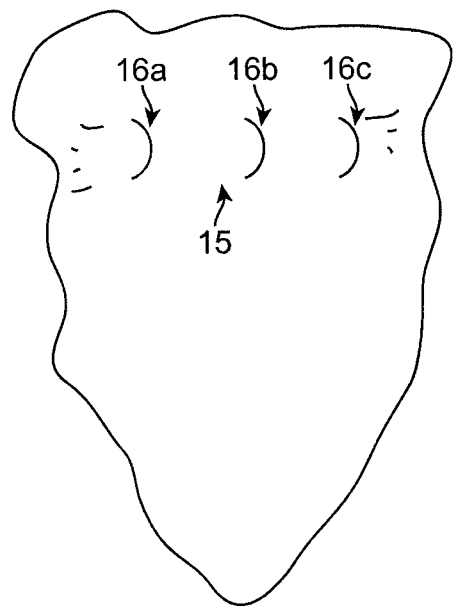
Figure 1E:
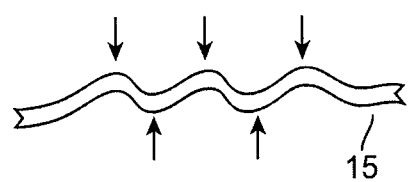

As noted, various designs, orientations, and/or configurations of shaped features are available for use according to the present invention and can depend, at least partially, on the desired application of force and tooth movement. Exemplary designs/configurations of ridged protrusions are illustrated with reference to FIGS. 1B-1E. FIG. 1B illustrates a ridge 12 formed by a continuous protrusion in an appliance surface or a ridge. While the geometric features of ridge 12 may vary along the length, the ridge is continuous in the sense that it is configured to contact a tooth surface along an uninterrupted length. Ridge 12 is illustrated as having a more horizontal orientation relative to the tooth or, in other words, perpendicular to the tooth in the crown to root direction. Referring to FIG. 1C, a continuous ridge 14 is illustrated disposed in an appliance cavity in a vertical orientation. FIG. 1D illustrates a non-continuous ridge 15 that is disposed in an appliance surface and vertically oriented. FIG. 1E shows a cross-sectional view of ridge 15, illustrating the sort of corrugated surface forming the non-continuous ridge by a series of dimples or bump-like protrusions 16a, 16b, 16c. As illustrated, such bump-like protrusions can each include a portion of the protrusion that contacts a tooth surface, with each tooth contacting surface of a protrusion separated by non-tooth contacting regions of the ridge having a different height. Parameters of tooth contacting and non-contacting aspects of a non-continuous ridge, as illustrated, can be defined, as least in part, by fabrication methods (e.g., direct fabrication, vacuum molding, etc.) used. Both continuous and non-continuous type ridges function to apply a force vector along a length of the tooth, rather than at a single point as with a single dimple or bump-like protrusion. Shaped features, such as ridges can be designed in various shapes (e.g., curve, "L" shaped, "T" shaped, hook, etc.), as well as orientations (e.g., vertical, horizontal, slanted, etc.) and are not limited to any particular shape or orientation.

Any number of one or more shaped features can be included in design and fabrication of an improved appliance of the present invention. In one embodiment, a cavity of an appliance can include a plurality of shaped features, such as protrusions. For example, a cavity can include at least two shaped features such as protrusions that are shaped and positioned within the cavity such that each of the protrusions are brought into contact with the received patient's tooth when the appliance is initially worn by the patient. Thus, a number of protrusions (e.g., two or more) can configured and incorporated in appliance such that each of those protrusions will each engage the received tooth when the appliance is initially worn by the patient and before the tooth has been moved by the appliance.

Besides protrusions or non-attachment type shaped features, the shaped features of the present invention can optionally include attachment type features. Attachment, as used herein, may be any form of material that may be attached to the tooth whether preformed, formed using a template or in an amorphous form that is attached to the surface of the tooth. It can be disposed on the tooth surface using an adhesive material, or the adhesive material itself may be disposed on the surface of the tooth as an attachment.

Generally, the attachments operate to provide "bumps" on a surface of the tooth which otherwise would be difficult for the dental appliance to grip. Attachments may also be engaged by the appliance in a manner that favors delivery of desired force directions and magnitudes. Attachments typically include a material bonded or attached to a surface of the tooth, with a corresponding receiving portion or couple built into the tooth receiving appliance. In one example, an attachment-type feature can include an orphan attachment, or any appropriate shaped material bonded to crown surface, but with no receptacle or receiving portion built into the appliance to receive the attachment shape. Instead, the generated force concentrates on contact area between appliance surface and attachment.

Various tooth movements can be accomplished according to the present invention. Examples of specific movements that can be included and which are further described below include translation, such as buccal-labial lingual translation, mesio-distal translation, extrusion, intrusion, root movements, first order rotation, second order root movement, and third order root movement. However, the methods can be applied to achieve any type of tooth movement, in any direction, in any arbitrary plane of space.

Non-attachment type shaped features or protrusions can be included in the present invention, and may optionally be utilized in conjunction with use of attachment type features as described above. In some instances, such protrusions can be described in an analogous manner to description in regard to attachments, for example, in terms positioning and application of selected forces to a tooth. In certain aspects, however, use of protrusion features (e.g., ridge-like protrusions) can provide numerous differences and/or advantages compared to use of attachments.

In still another aspect, the aligner features may be designed and fabricated to limit movement of the tooth. For example, the aligner may be designed to be a physical boundary through which the tooth cannot move providing safety against unwanted movements that may be deleterious to the patient's health. Further, the aligner in another aspect may be configured to function as a guiding surface along which the tooth moves. More particularly, the aligner may be configured to impart a force system to the tooth and the tooth may be guided into a specific location and orientation assisted by the guidance of the aligner.

As set forth above, incorporation of one or more protrusions in appliance design according to the present invention can be utilized for various tooth movements. Non-limiting examples of specific movements that can be accomplished and which are further described below include translation, such as buccal-labial lingual translation, mesio-distal translation, extrusion, intrusion, first order rotation, second order root movement, and third order root movement. Exemplary tooth movements and corresponding positioning of shaped features are described below with reference to corresponding figures (see, e.g., FIGS. 2A-2F, 3A-3D, 4A-4C, and 5A-5B).

Buccal-Lingual Translation

Figure 2A:
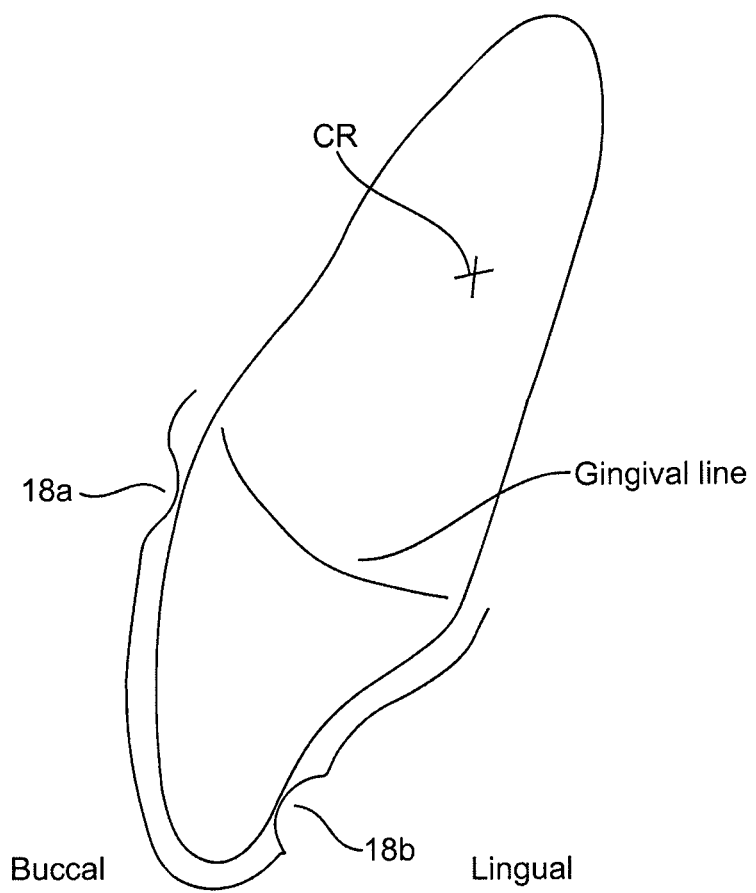
FIGS. 2A-2F illustrate positioning of shaped features for buccal-lingual translation, according to an embodiment of the present invention.
Figure 2B:
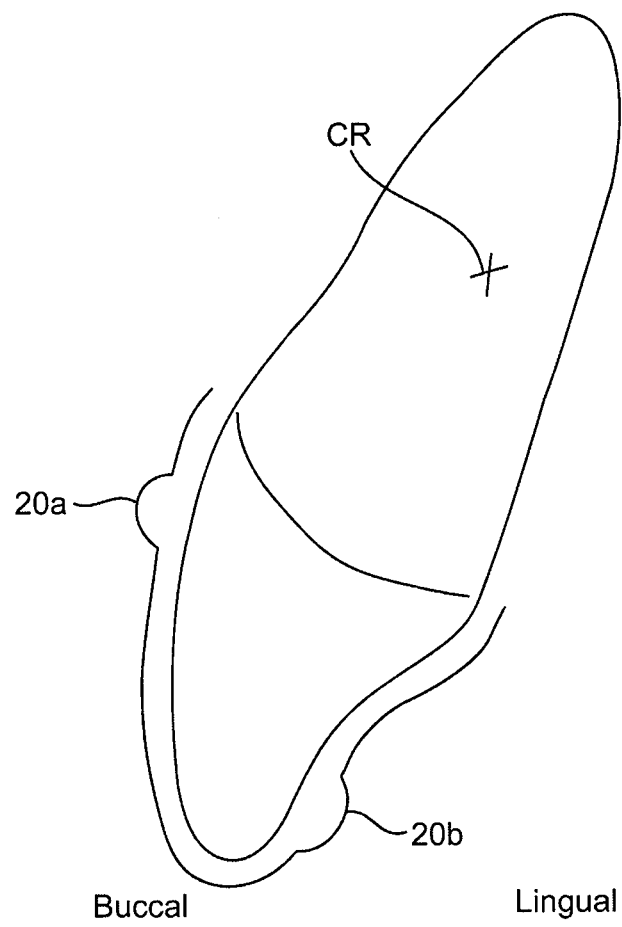
Figure 2C:
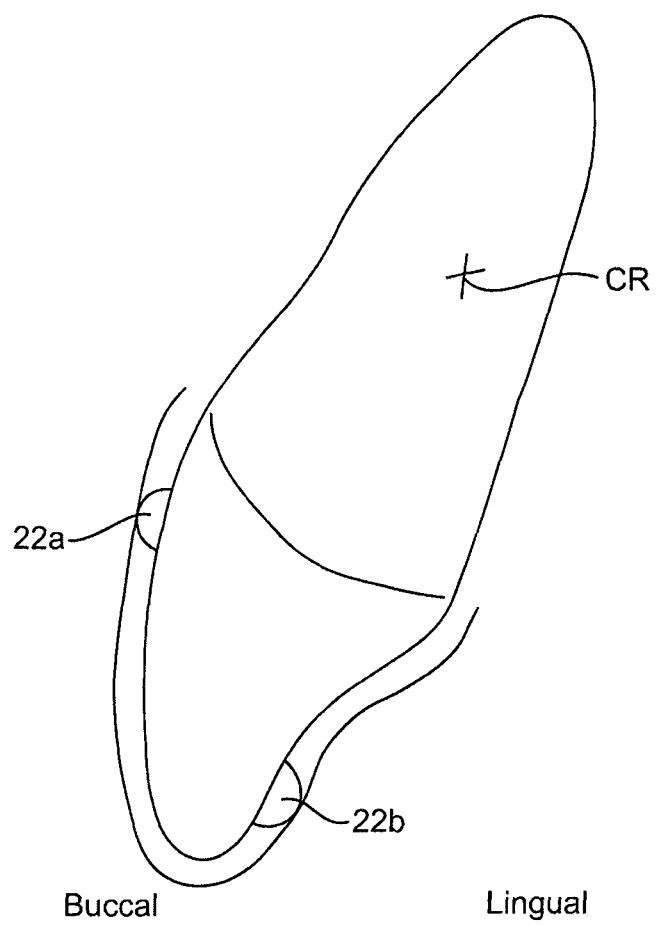

Shaped features, including protrusions or ridge shaped features can be used for tooth translation, such as buccal or lingual translation. FIGS. 2A-2F illustrate an appliance positioned on a tooth receiving cavity of the appliance including shaped feature(s) positioning for lingual translation. Illustrated shaped features include appliance protrusions, orphan attachments, or a combination thereof. As illustrated, to achieve lingual translation, features on the buccal side are closer the gingival line than the features on the lingual side. Stated another way, attachment to center of resistance (CR) length is greater on the lingual side compared to the buccal side. FIG. 2A shows interior ridge features are added to an appliance, including an interior ridge 18a on the buccal side and positioned closer to the gingival line (or to the center of resistance), and an interior ridge 18b on the lingual side and positioned more distally compared to the buccal side ridge 18a. The parameters of the features will be selected and designed such that the lingual force generated from buccal features will be greater than the buccal force from the lingual features. However, the directions of these two force components are opposite. The lingual force has longer arm to the center of resistance than the buccal force does. By adjusting the positions and parameters of the buccal and lingual features, the tipping moment from buccal features can be cancelled out by the counter balancing moment from lingual features and the resultant is the lingual translation. FIG. 2B and FIG. 2C illustrate a similar concept, but with use of shaped features in the forms of exterior ridges 20a, 20b (FIG. 2B) and orphan attachments 22a, 22b (FIG. 2C) used for lingual translation.

Figure 2D:
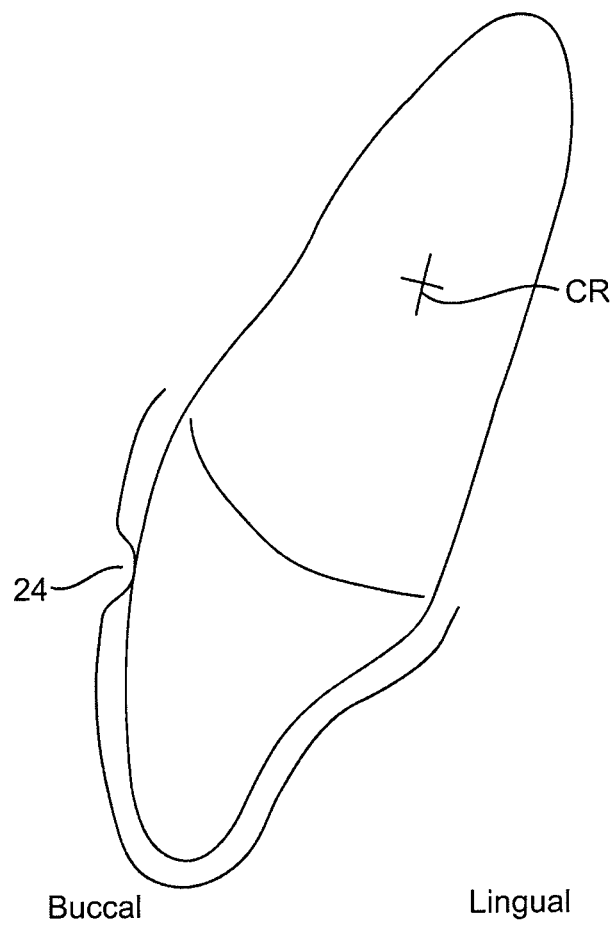
Figure 2E:
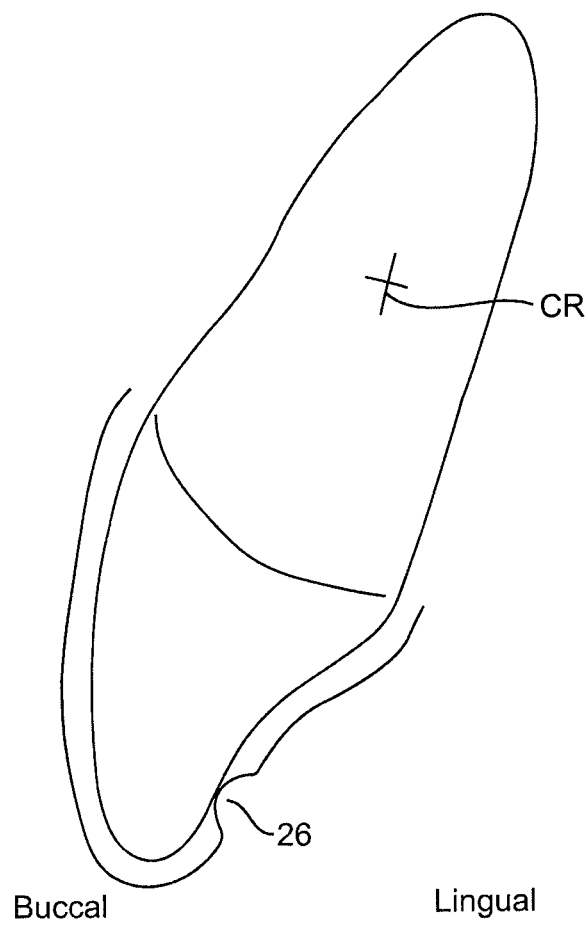

In certain embodiments, a tooth receiving cavity may include only a single protrusion or ridge-shaped feature. FIGS. 2D through 2E illustrate use of a single protrusion for lingual translation. If there is no feature added to the buccal side of aligner, the buccal surface of aligner will generate a translation force toward lingual direction. In another embodiment, a feature can be added to lingual side alone to create a counter balance torque to the force generated from an appliance surface in contact with the tooth on the opposing buccal side. FIG. 2D illustrates a single protrusion feature 24 positioned on the buccal side to impart a lingual force and illicit a counter balance torque from the contact between the tooth and appliance. FIG. 2E shows a single protrusion feature 26 in the form of interior ridge on lingual side only of appliance cavity.

Figure 2F:
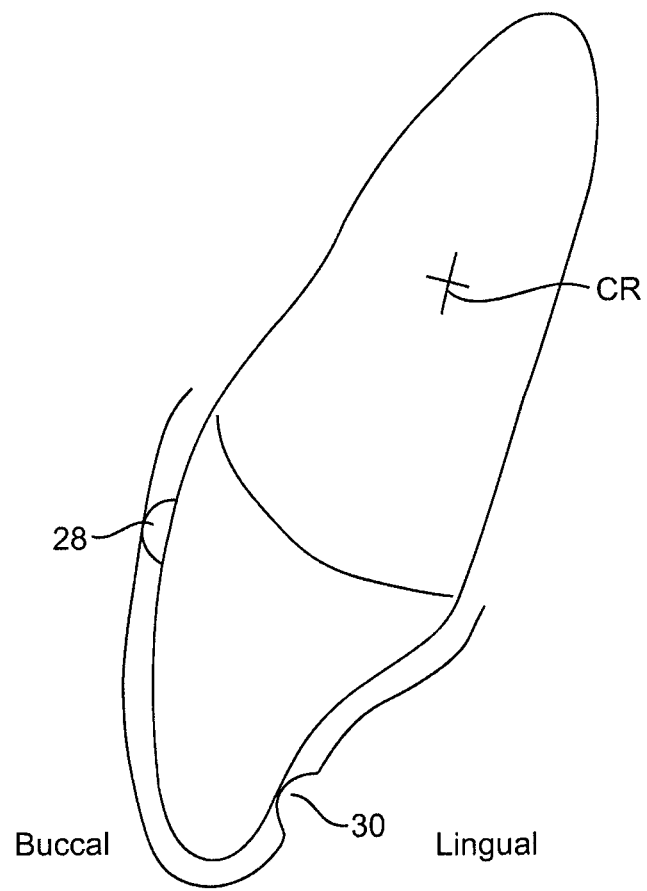

In another embodiment, a single protrusion can be used in conjunction with an attachment-type feature for the desired tooth movement. FIG. 2F shows a buccal side orphan attachment 28 used with interior ridge 30 on lingual side of the appliance cavity. The various different shapes and types of features and protrusions can be utilized and/or combined to accomplish lingual translation as described above.

Protrusion and shaped feature use can by selected for buccal translation and feature positioning can be selected in a manner analogous to the above description regarding lingual translation (e.g., FIGS. 2A-2F). In contrast to lingual translation, use of features for buccal translation will include positioning of a lingual side feature or component closer to the gingival line relative to buccal side feature/component placement.

Mesial-Distal Translation

Figure 3A:
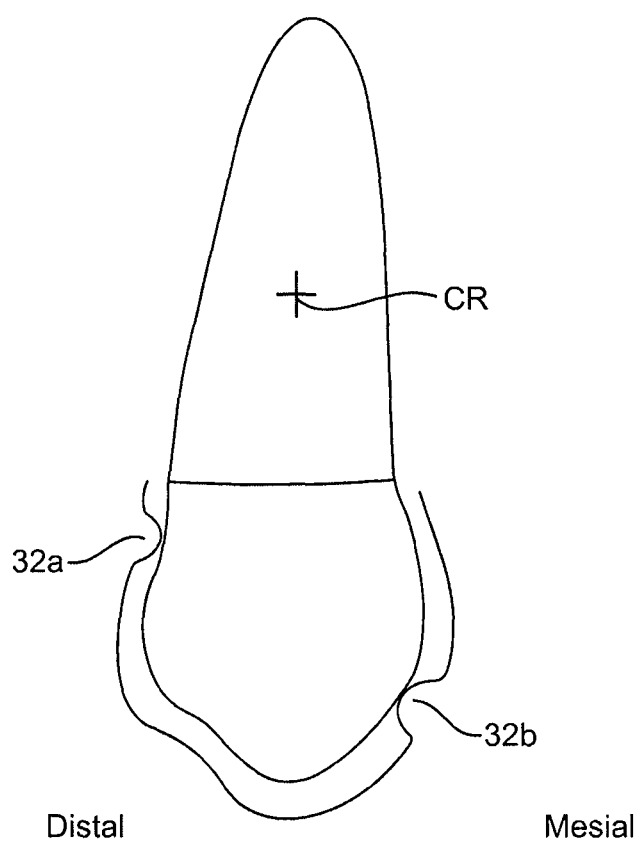
FIGS. 3A-3D illustrate positioning of shaped features for distal-mesial translation, according to an embodiment of the present invention.
Figure 3B:
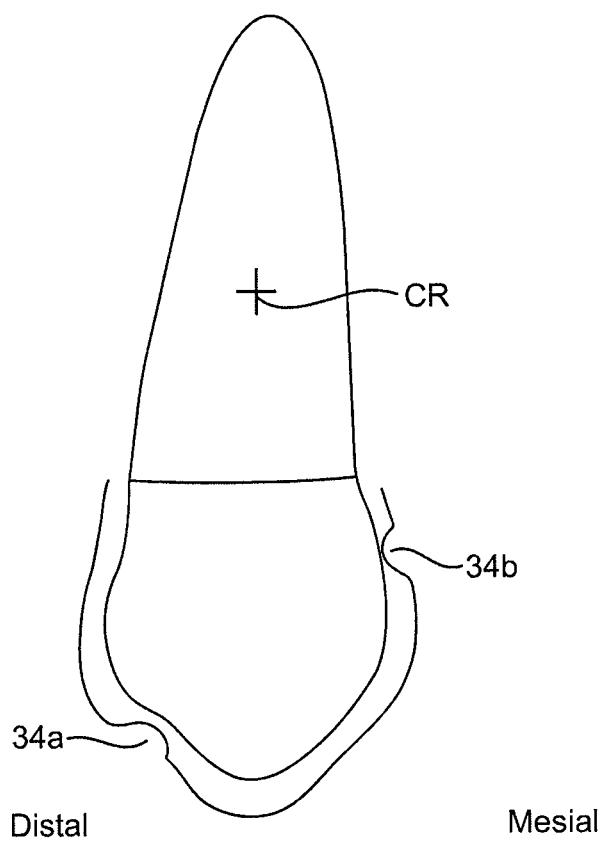
Figure 3C:
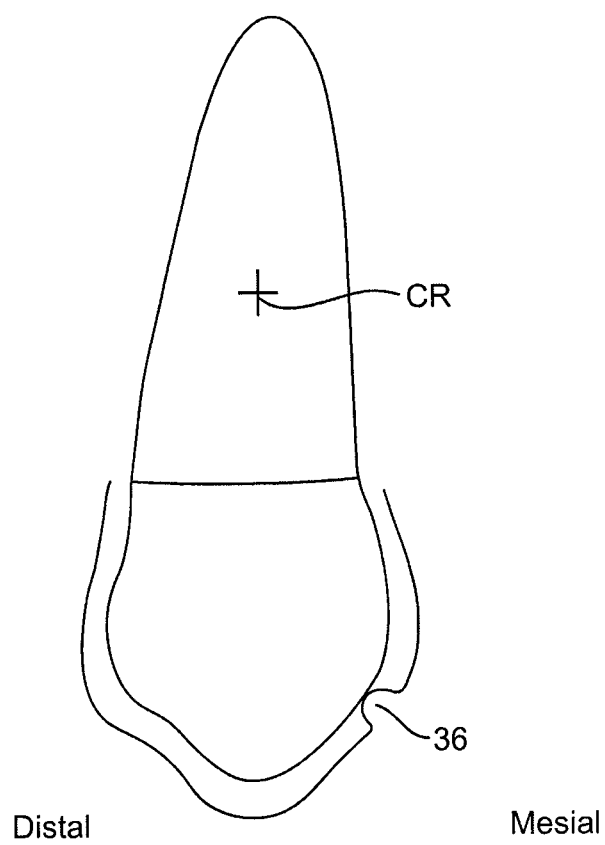
Figure 3D:
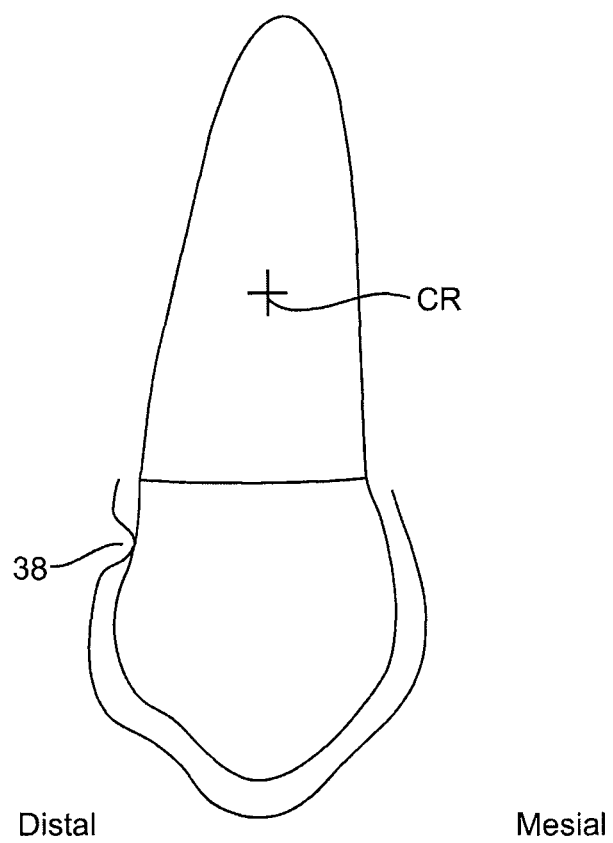

In another aspect, shaped features are used to accomplish mesial or distal translation. As seen in FIG. 3A, where the desired movement includes mesial translation, features (e.g., ridges) such as Feature 32a on the distal interproximal area will be positioned closer to the gingival line compared to features on the mesial interproximal area such as Feature 32b, while features on the mesial interproximal area will be closer to the occlusal plane. By controlling the parameters and positions of features, the selected forces can include a mesial force exceeding the distal force and the second order moment can be zeroed out. Spacing or room around the interproximal area can be created in the patient's dentition to accommodate the features of the appliance. In some embodiments, a single feature only may be included or features positioned only on a distal area or mesial area. FIG. 3C show the Features 36 positioned only on mesial surface for distal translation. FIG. 3D illustrates Features 38 positioned only on the distal surface for mesial translation.

Distal translation can be accomplished in a manner analogous to the above description regarding mesial translation, but with features on the mesial interproximal area positioned closer to the gingival line compared to features on the distal interproximal area, with features on the distal interproximal area positioned closer to the occlusal plane. FIG. 3B illustrates Features 34a, 34b positioning selected for distal translation.

Extrusion and Intrusion

Figure 4A:
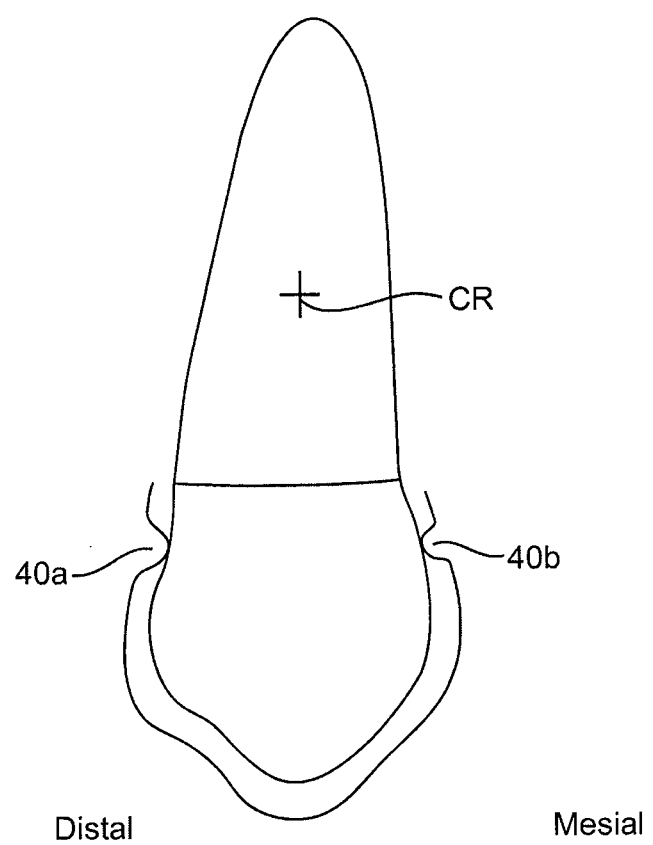
FIGS. 4A-4C illustrate positioning of shaped features for extrusion-intrusion movements, according to an embodiment of the present invention.
Figure 4B:
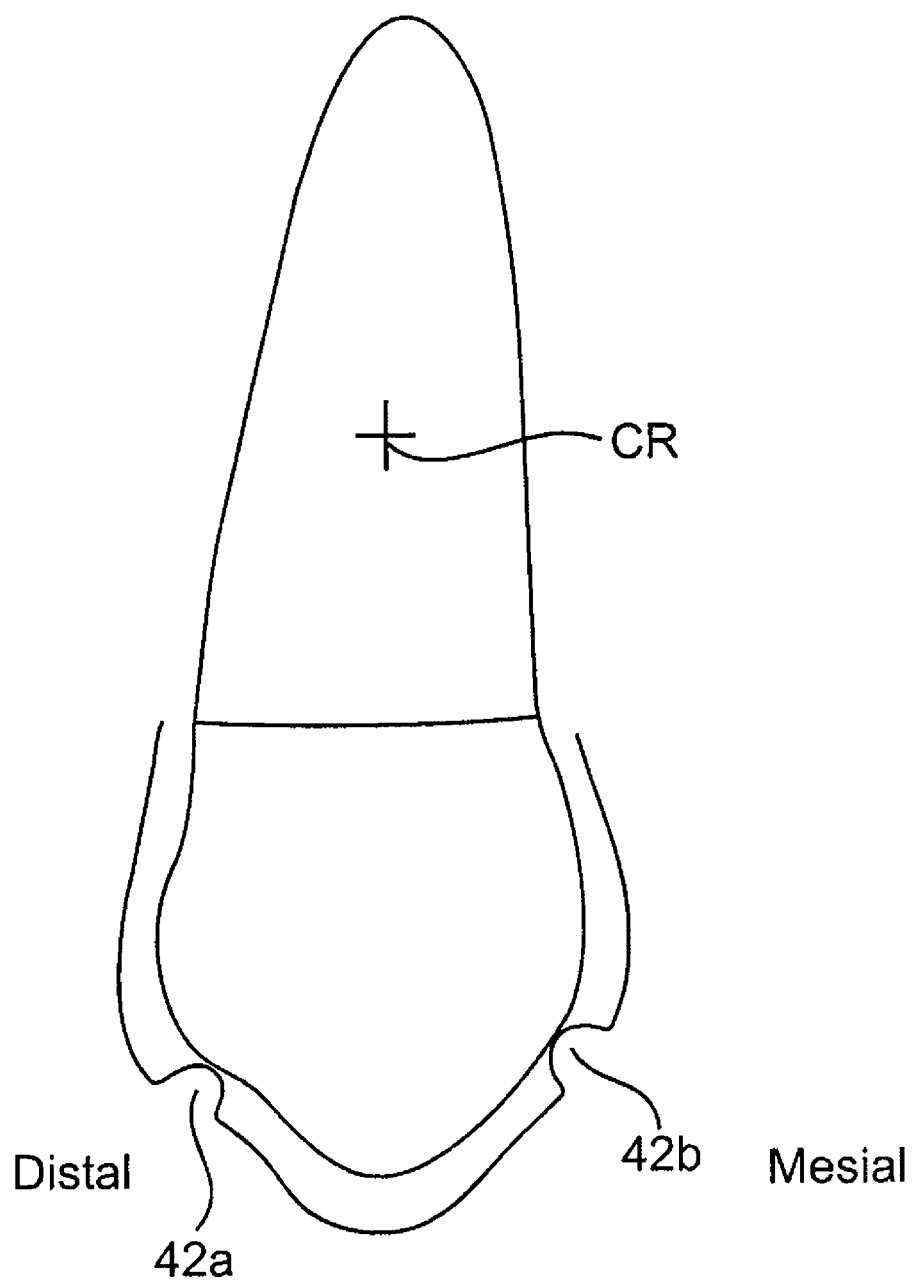
Figure 4C:
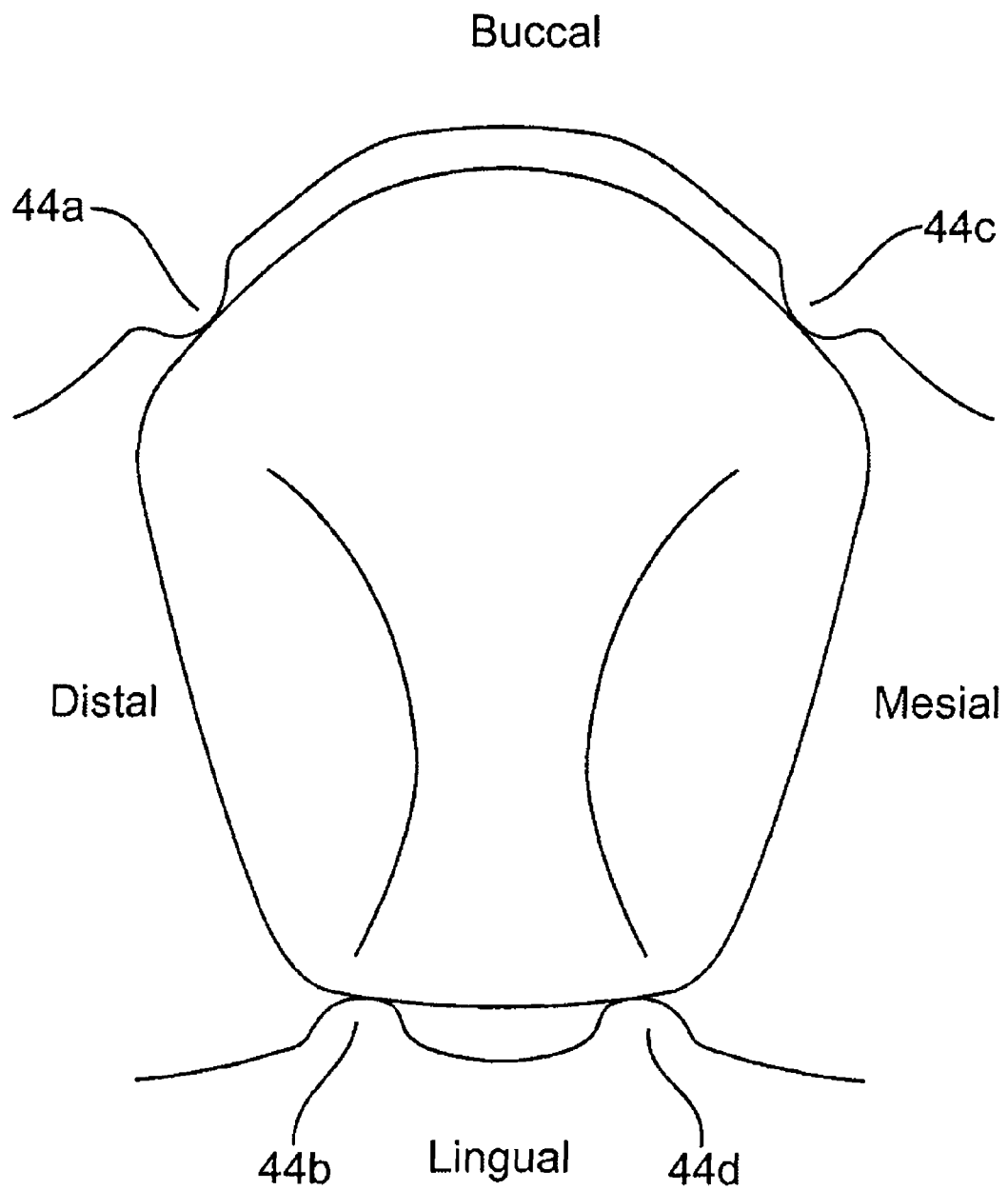

In another aspect, feature design and positioning can be selected for extrusion and intrusion movements, as illustrated in FIGS. 4A-4C. For extrusion, for example, features on appliance cavity can be positioned toward the gingival line, as the buccal and lingual surfaces in the gingival half of the crown are usually undercut, as shown in FIGS. 4A (Features 40a, 40b) and 4C (Features 44a, 44b, 44c, 44d). By selecting the parameters and positions of the features, the undercutting contact areas can provide total contact force extrusive, because the forces from each feature will be normal to the undercutting contact area.

For intrusion, the features on aligner can be selected and positioned closer toward the occlusal plane as the buccal and lingual surfaces in the occlusal half of the crown are usually convex, as shown in FIGS. 4B (Features 42a, 42b) and 4C (Features 44a, 44b, 44c, 44d). By tuning the parameters and positions of the features, the convex contact areas can provide total contact force intrusive, as the forces from each feature will be normal to the contact area.

Third Order Root Movement

In another aspect, as will be recognized, use of features as described herein can be directed to various root movements. When a third order root movement (e.g., lingual root torque) is desired on tooth crown, the crown will rotate buccally much less than the root will rotate lingually. The features on the buccal side can be positioned closer to gingival line and the ones on lingual side are closer to occlusal plane (e.g., as shown in FIG. 2A). In such an instance, the features on the buccal side will generate lingual force and the lingual features will generate buccal force. By configuring the parameters and positions of features, feature positioning can be selected such that the lingual force exceeds buccal force. However, the directions of these two forces are opposite, with the lingual force having a longer arm to the center of resistance than the buccal force. By adjusting the positions and parameters of the buccal and lingual features, feature design/positioning can be selected such that the lingual features generate torquing moment greater than the buccal features, which combined with lingual total force results in lingual root torque. As illustrated in FIG. 2D, buccal surface only features may be selected, without features on lingual surface of appliance cavity. A similar mechanism as described above applies, now that the lingual surface of plain (e.g., no feature) appliance cavity surface works in place of lingual features. Buccal root torque can be figured out in an analogous manner.

Second Order Root Movement

In another aspect, second order root movements can be accomplished. In one embodiment, for a second order mesial root movement, cavity design can be selected such that features on the distal interproximal area will be closer to the gingival line, while features on the mesial interproximal area will be closer to the occlusal plane (e.g., FIG. 3A). By controlling the parameters and positions of features, the mesial force prevails. However, the directions of these two forces from the two illustrated features are opposite, with the distal force having a longer arm to the center of resistance than the mesial force. By adjusting the positions and parameters of the mesial and distal features, the mesial features generate second order moment greater than the force generated by the distal features, which combined with mesial total force results in a second order root movement.

As above, features may be present only on one side of the appliance cavity. For example, FIG. 3D shows features only on a distal surface for second order mesial root movement. The same mechanism still applies as described above, now that the mesial surface of plain aligner works in place of mesial features.

Second order distal root movement can be figured out in an analogous manner as described with regard to second order mesial root movement, but with features on the distal interproximal area positioned closer to the occlusal plan (see, e.g., FIG. 4B).

First Order Rotation

Figure 5A:
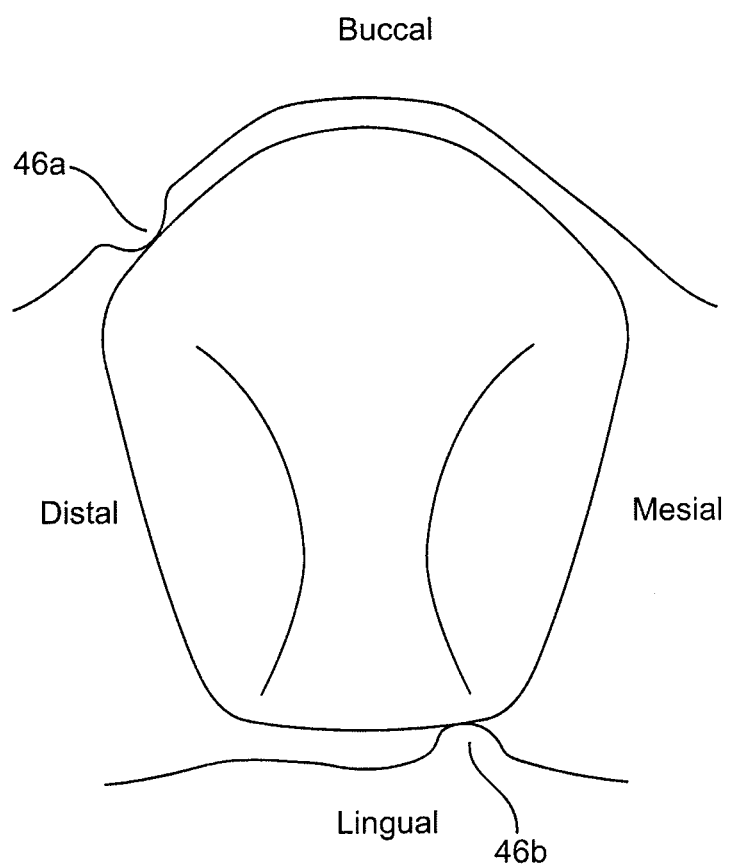
FIGS. 5A-5B illustrate positioning of shaped features for tooth rotations, according to an embodiment of the present invention.
Figure 5B:
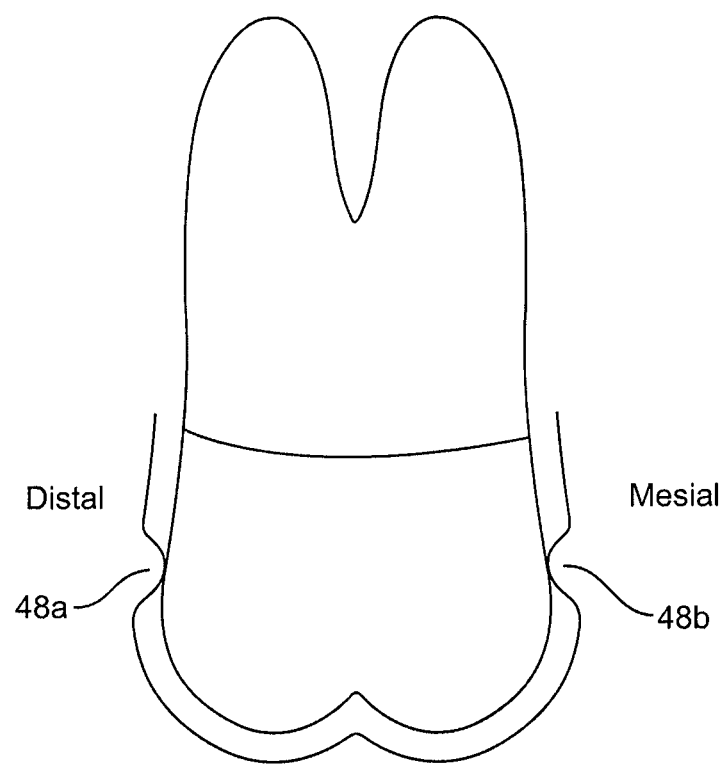

In another aspect, first order rotations can be selected. In one embodiment of a first order rotation, the parameters and positions of features will be configured to provide a couple about the occlusal gingival direction, as shown in FIGS. 5A (e.g., Features 46a, 46b) and 5B (e.g., Features 48a, 48b). A couple is a moment generated by a pair of forces oriented parallel to one another, equal in magnitude and opposite in sense. The resultant force is zero.

As described above, a patient's teeth are generally progressively repositioned according to a treatment plan. Exemplary methods treatment plan design, as well as appliance design and fabrication are described further below. Typically, appliance and/or treatment plan can optionally, though not necessarily, be accomplished using various computer based applications. It will be recognized that appliance design and fabrication is not limited to any particular method and can include various computer and non-computer based methodologies.

Treatment planning, according to one embodiment of the present invention, is described. Patient data can be collected and analyzed, and specific treatment steps specified and/or prescribed. In one embodiment, a treatment plan can be generated and proposed for a dental practitioner to review. The dental practitioner can accept or request modifications to the treatment plan. Once the treatment plan is approved, manufacturing of appliance(s) can begin. Digital treatment plans are now possible with 3-dimensional orthodontic treatment planning tools such as software from Align Technology, Inc. or other software available from eModels and OrthoCAD, among others. These technologies allow the clinician to use the actual patient's dentition as a starting point for customizing the treatment plan. The software technology available from Align Technology, Inc., uses a patient-specific digital model to plot a treatment plan, and then use a scan of the achieved or actual treatment outcome to assess the degree of success of the outcome as compared to the original digital treatment plan as discussed in U.S. patent application Ser. No. 10/640,439, filed Aug. 21, 2003 and U.S. patent application Ser. No. 10/225,889 filed Aug. 22, 2002. The problem with the digital treatment plan and outcome assessment is the abundance of data and the lack of standards and efficient methodology by which to assess "treatment success" at an individual patient level. To analyze the information, a dental data mining system is used.

Figure 6A:
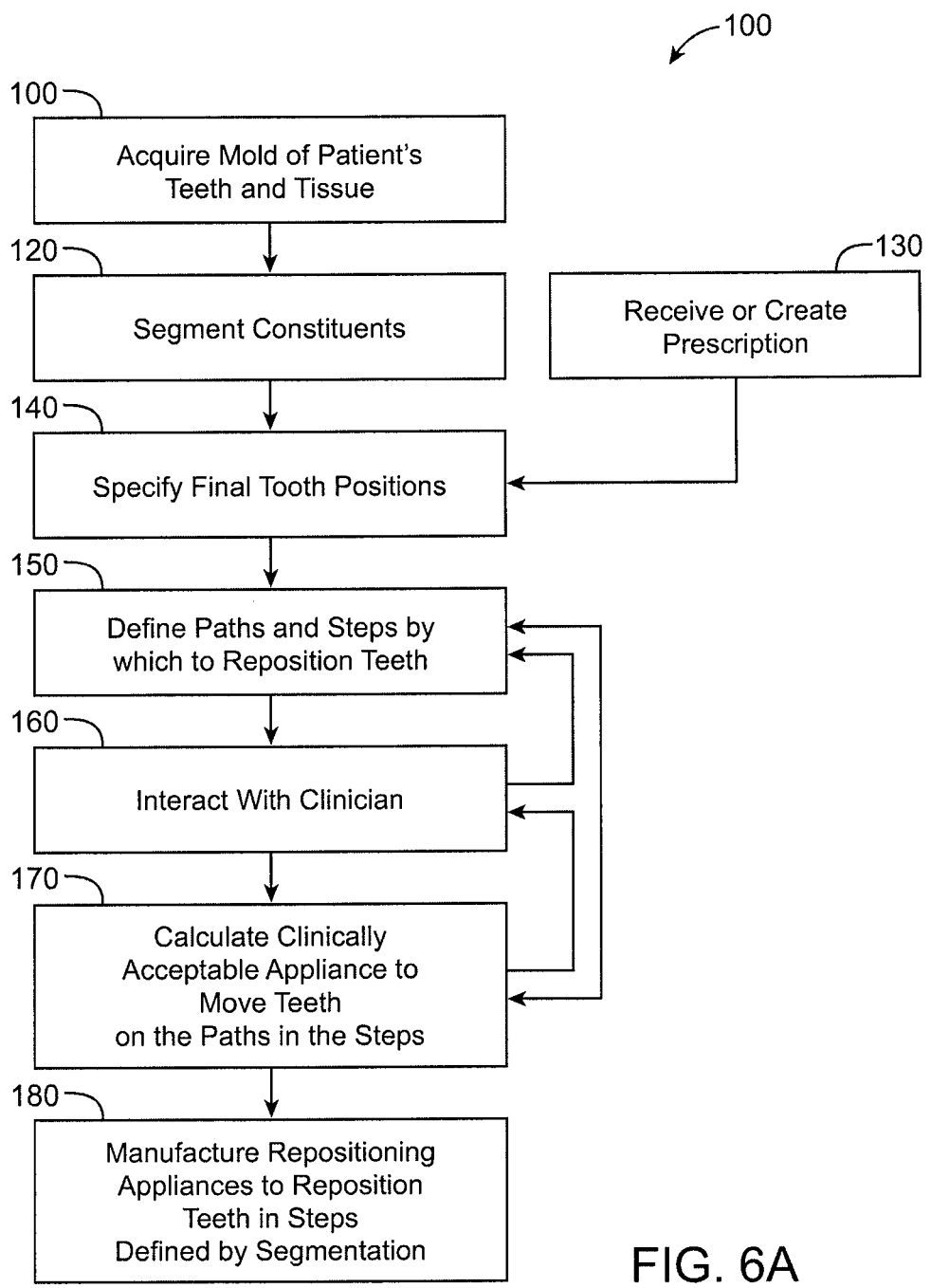
FIG. 6A is a flowchart of a process of specifying a course of treatment including a subprocess for calculating aligner shapes in accordance with the invention, according to an embodiment of the present invention.

FIG. 6A illustrates the general flow of an exemplary process 100 for generating a treatment plan or defining and generating repositioning appliances for orthodontic treatment of a patient. The process 100 includes the methods, and is suitable for the apparatus, of the present invention, as will be described. The computational steps of the process are advantageously implemented as computer program modules for execution on one or more conventional digital computers.

As an initial step, a mold or a scan of patient's teeth or mouth tissue is acquired (110). This step generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to segment the tissue constituents from each other (step 120). In particular, in this step, data structures that digitally represent individual tooth crowns are produced. Advantageously, digital models of entire teeth are produced, including measured or extrapolated hidden surfaces and root structures as well as surrounding bone and soft tissue.

The desired final position of the teeth—that is, the desired and intended end result of orthodontic treatment—can be received from a clinician in the form of a prescription, can be calculated from basic orthodontic principles, or can be extrapolated computationally from a clinical prescription (step 130). With a specification of the desired final positions of the teeth and a digital representation of the teeth themselves, the final position and surface geometry of each tooth can be specified (step 140) to form a complete model of the teeth at the desired end of treatment. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a final position for each tooth, the process next defines a tooth path for the motion of each tooth. In one embodiment, the tooth paths are optimized in the aggregate so that the teeth are moved in the quickest fashion with the least amount of round-tripping to bring the teeth from their initial positions to their desired final positions. (Round-tripping is any motion of a tooth in any direction other than directly toward the desired final position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (step 170, described later), which may determine that at one or more points along one or more tooth paths, the forces that can be generated by the appliance on the then-existing configuration of teeth and tissue is incapable of effecting the repositioning that is represented by one or more tooth path segments. With this information, the subprocess defining segmented paths (step 150) can recalculate the paths or the affected subpaths.

At various stages of the process, and in particular after the segmented paths have been defined, the process can, and generally will, interact with a clinician responsible for the treatment of the patient (step 160). Clinician interaction can be implemented using a client process programmed to receive tooth positions and models, as well as path information from a server computer or process in which other steps of process 100 are implemented. The client process is advantageously programmed to allow the clinician to display an animation of the positions and paths and to allow the clinician to reset the final positions of one or more of the teeth and to specify constraints to be applied to the segmented paths. If the clinician makes any such changes, the subprocess of defining segmented paths (step 150) is performed again.

The segmented tooth paths and associated tooth position data are used to calculate clinically acceptable appliance configurations (or successive changes in appliance configuration) that will move the teeth on the defined treatment path in the steps specified by the path segments (step 170). Each appliance configuration represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (step 160). The operation of a process step 200 implementing this step will be described more fully below.

Having calculated appliance definitions, the process 100 can proceed to the manufacturing step (step 180) in which appliances defined by the process are manufactured, or electronic or printed information is produced that can be used by a manual or automated process to define appliance configurations or changes to appliance configurations.

Figure 6B:
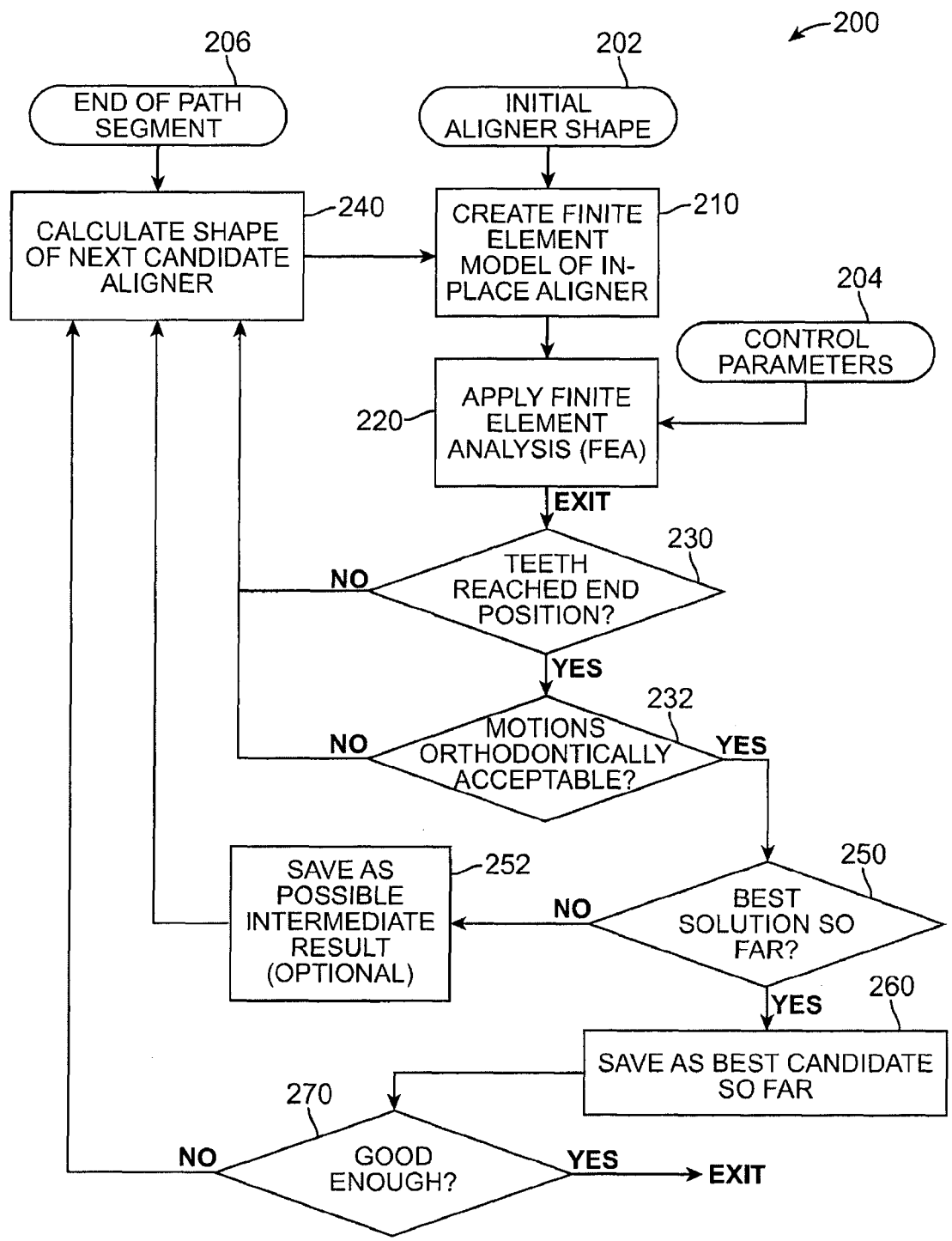
FIG. 6B is a flowchart of a process for calculating aligner shapes, according to an embodiment of the present invention.

FIG. 6B illustrates a process 200 implementing the appliance-calculation step (FIG. 6A, step 170) for polymeric shell aligners of the kind described in above-mentioned U.S. Pat. No. 5,975,893. Inputs to the process include an initial aligner shape 202, various control parameters 204, and a desired end configuration for the teeth at the end of the current treatment path segment 206. Other inputs include digital models of the teeth in position in the jaw, models of the jaw tissue, and specifications of an initial aligner shape and of the aligner material. Using the input data, the process creates a finite element model of the aligner, teeth and tissue, with the aligner in place on the teeth (step 210). Next, the process applies a finite element analysis to the composite finite element model of aligner, teeth and tissue (step 220). The analysis runs until an exit condition is reached, at which time the process evaluates whether the teeth have reached the desired end position for the current path segment, or a position sufficiently close to the desired end position (step 230). If an acceptable end position is not reached by the teeth, the process calculates a new candidate aligner shape (step 240). If an acceptable end position is reached, the motions of the teeth calculated by the finite elements analysis are evaluated to determine whether they are orthodontically acceptable (step 232). If they are not, the process also proceeds to calculate a new candidate aligner shape (step 240). If the motions are orthodontically acceptable and the teeth have reached an acceptable position, the current aligner shape is compared to the previously calculated aligner shapes. If the current shape is the best solution so far (decision step 250), it is saved as the best candidate so far (step 260). If not, it is saved in an optional step as a possible intermediate result (step 252). If the current aligner shape is the best candidate so far, the process determines whether it is good enough to be accepted (decision step 270). If it is, the process exits. Otherwise, the process continues and calculates another candidate shape (step 240) for analysis.

The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Mass., the I-DEAS design software products available from Structural Dynamics Research Corporation (SDRC) of Cincinnati, Ohio, and the MSC/NASTRAN product available from Mac-Neal-Schwendler Corporation of Los Angeles, Calif.

Figure 7:
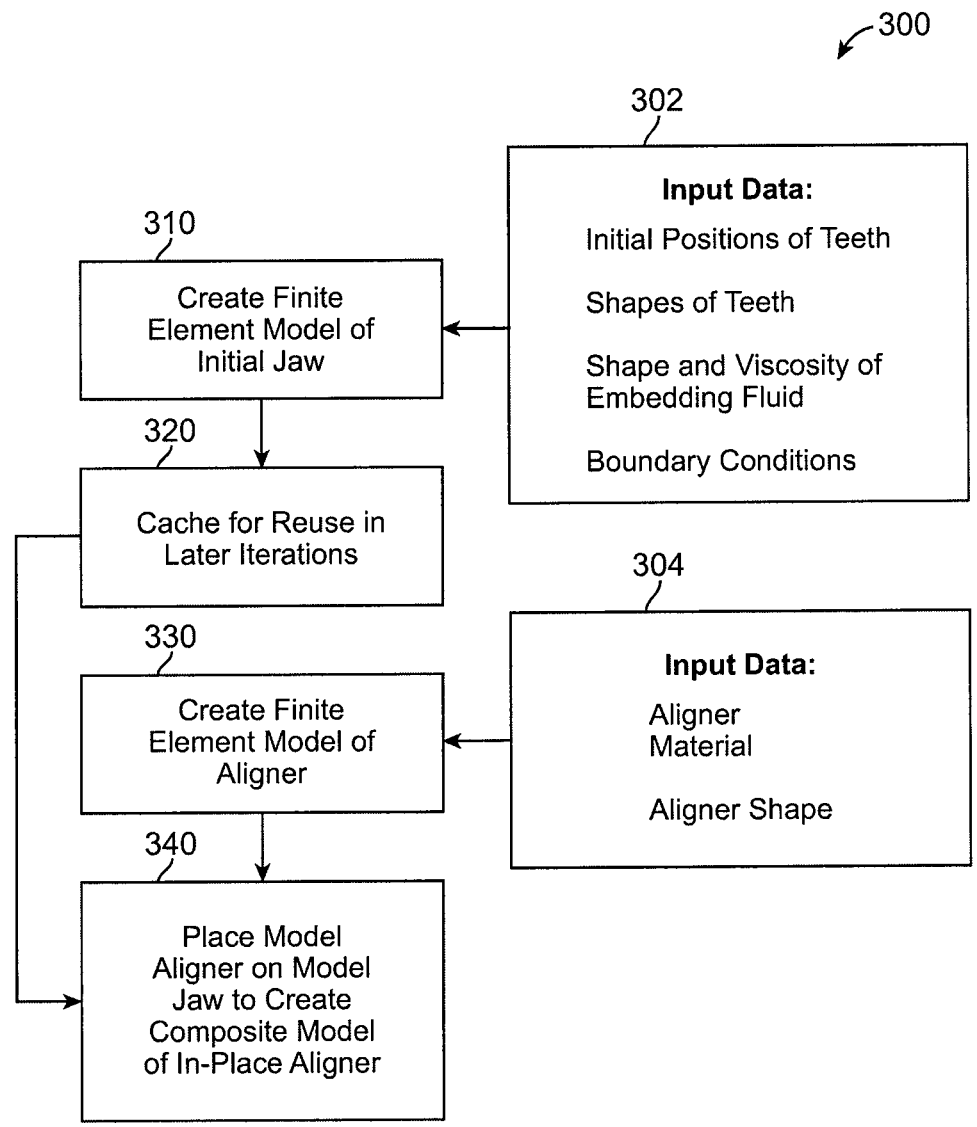
FIG. 7 is a flowchart of a subprocess for creating finite element models, according to an embodiment of the present invention.

FIG. 7 shows a process 300 of creating a finite element model that can be used to perform step 210 of the process 200 (FIG. 6B). Input to the model creation process 300 includes input data 302 describing the teeth and tissues and input data 304 describing the aligner. The input data describing the teeth 302 include the digital models of the teeth; digital models of rigid tissue structures, if available; shape and viscosity specifications for a highly viscous fluid modeling the substrate tissue in which the teeth are embedded and to which the teeth are connected, in the absence of specific models of those tissues; and boundary conditions specifying the immovable boundaries of the model elements. In one implementation, the model elements include only models of the teeth, a model of a highly viscous embedding substrate fluid, and boundary conditions that define, in effect, a rigid container in which the modeled fluid is held. Note that fluid characteristics may differ by patient clusters, for example as a function of age.

A finite element model of the initial configuration of the teeth and tissue is created (step 310) and optionally cached for reuse in later iterations of the process (step 320). As was done with the teeth and tissue, a finite element model is created of the polymeric shell aligner (step 330). The input data for this model includes data specifying the material of which the aligner is made and the shape of the aligner (data input 304).

The model aligner is then computationally manipulated to place it over the modeled teeth in the model jaw to create a composite model of an in-place aligner (step 340). Optionally, the forces required to deform the aligner to fit over the teeth, including any hardware attached to the teeth, are computed and used as a figure of merit in measuring the acceptability of the particular aligner configuration. Optionally, the tooth positions used are as estimated from a probabilistic model based on prior treatment steps and other patient information. In a simpler alternative, however, the aligner deformation is modeled by applying enough force to its insides to make it large enough to fit over the teeth, placing the model aligner over the model teeth in the composite model, setting the conditions of the model teeth and tissue to be infinitely rigid, and allowing the model aligner to relax into position over the fixed teeth. The surfaces of the aligner and the teeth are modeled to interact without friction at this stage, so that the aligner model achieves the correct initial configuration over the model teeth before finite element analysis is begun to find a solution to the composite model and compute the movement of the teeth under the influence of the distorted aligner.

Figure 8:
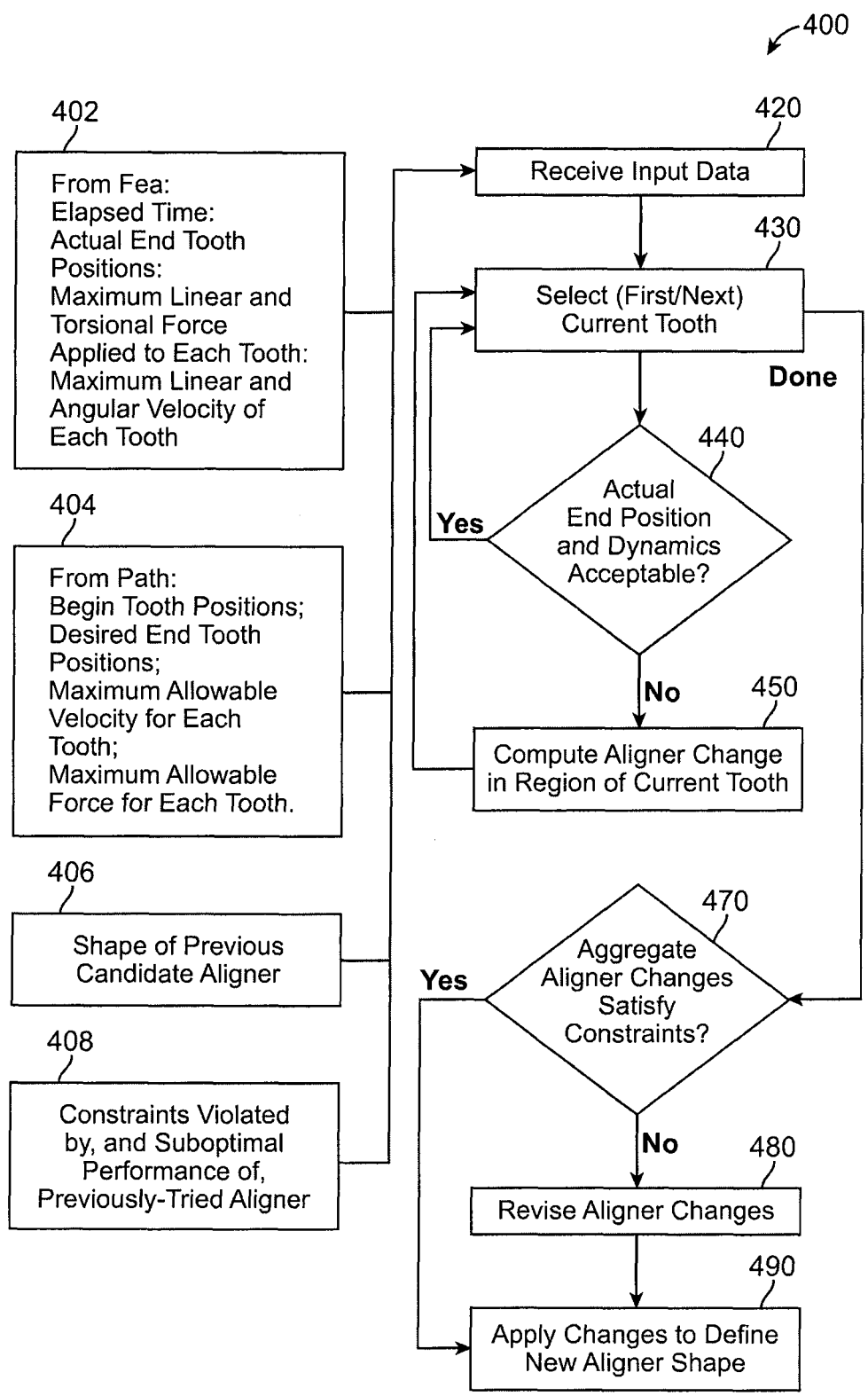
FIG. 8 is a flowchart of a subprocess for computing aligner changes, according to an embodiment of the present invention.

FIG. 8 shows a process 400 for calculating the shape of a next aligner that can be used in the aligner calculations, step 240 of process 200 (FIG. 6B). A variety of inputs are used to calculate the next candidate aligner shape. These include inputs 402 of data generated by the finite element analysis solution of the composite model and data 404 defined by the current tooth path. The data 402 derived from the finite element analysis includes the amount of real elapsed time over which the simulated repositioning of the teeth took place; the actual end tooth positions calculated by the analysis; the maximum linear and torsional force applied to each tooth; the maximum linear and angular velocity of each tooth. From the input path information, the input data 404 includes the initial tooth positions for the current path segment, the desired tooth positions at the end of the current path segment, the maximum allowable displacement velocity for each tooth, and the maximum allowable force of each kind for each tooth.

If a previously evaluated aligner was found to violate one or more constraints, additional input data 406 can optionally be used by the process 400. This data 406 can include information identifying the constraints violated by, and any identified suboptimal performance of, the previously evaluated aligner. Additionally, input data 408 relating to constraints violated by, and suboptimal performance of previous dental devices can be used by the process 400.

Having received the initial input data (step 420), the process iterates over the movable teeth in the model. (Some of the teeth may be identified as, and constrained to be, immobile.) If the end position and dynamics of motion of the currently selected tooth by the previously selected aligner is acceptable ("yes" branch of decision step 440), the process continues by selecting for consideration a next tooth (step 430) until all teeth have been considered ("done" branch from step 430 to step 470). Otherwise ("no" branch from step 440), a change in the aligner is calculated in the region of the currently selected tooth (step 450). The process then moves back to select the next current tooth (step 430) as has been described.

When all of the teeth have been considered, the aggregate changes made to the aligner are evaluated against previously defined constraints (step 470), examples of which have already been mentioned. Constraints can be defined with reference to a variety of further considerations, such as manufacturability. For example, constraints can be defined to set a maximum or minimum thickness of the aligner material, or to set a maximum or minimum coverage of the aligner over the crowns of the teeth. If the aligner constraints are satisfied, the changes are applied to define a new aligner shape (step 490). Otherwise, the changes to the aligner are revised to satisfy the constraints (step 480), and the revised changes are applied to define the new aligner shape (step 490).

Figure 9A:
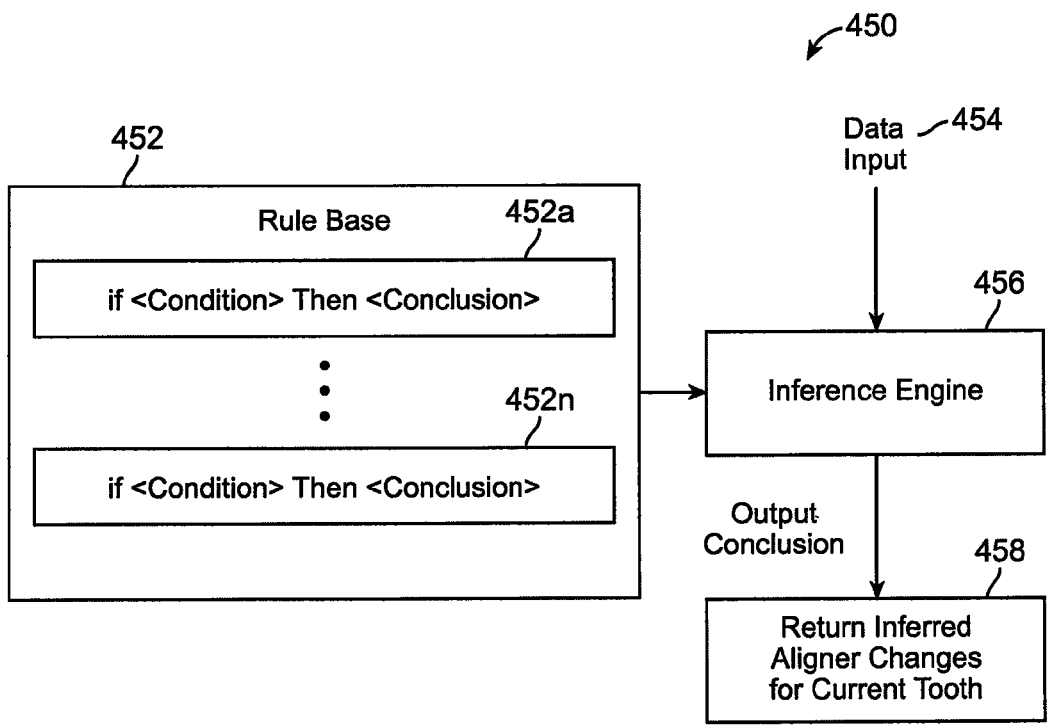
FIG. 9A is a flowchart of a subprocess for calculating changes in aligner shape, according to an embodiment of the present invention.

FIG. 9A illustrates one implementation of the step of computing an aligner change in a region of a current tooth (step 450). In this implementation, a rule-based inference engine 456 is used to process the input data previously described (input 454) and a set of rules 452*a*-452*n* in a rule base of rules 452. The inference engine 456 and the rules 452 define a production system which, when applied to the factual input data, produces a set of output conclusions that specify the changes to be made to the aligner in the region of the current tooth (output 458).

Rules 452*a* . . . 452*n* have the conventional two-part form: an if-part defining a condition and a then-part defining a conclusion or action that is asserted if the condition is satisfied. Conditions can be simple or they can be complex conjunctions or disjunctions of multiple assertions. An exemplary set of rules, which defines changes to be made to the aligner, includes the following: if the motion of the tooth is too fast, add driving material to the aligner opposite the desired direction of motion; if the motion of the tooth is too slow, add driving material to overcorrect the position of the tooth; if the tooth is too far short of the desired end position, add material to overcorrect; if the tooth has been moved too far past the desired end position, add material to stiffen the aligner where the tooth moves to meet it; if a maximum amount of driving material has been added, add material to overcorrect the repositioning of the tooth and do not add driving material; if the motion of the tooth is in a direction other than the desired direction, remove and add material so as to redirect the tooth.

Figure 9B:
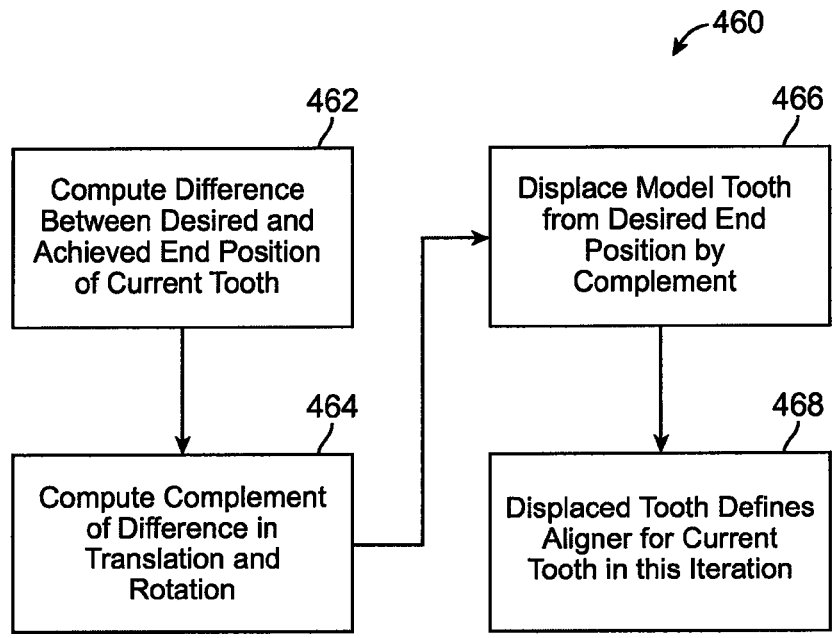
FIG. 9B is a flowchart of a subprocess for calculating changes in aligner shape, according to an embodiment of the present invention.
Figure 9C:
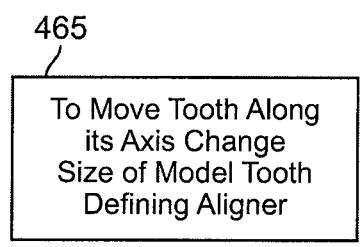
FIG. 9C is a flowchart of a subprocess for calculating changes in aligner shape, according to an embodiment of the present invention.

In an alternative embodiment, illustrated in FIGS. 9B and 9C, an absolute configuration of the aligner is computed, rather than an incremental difference. As shown in FIG. 9B, a process 460 computes an absolute configuration for an aligner in a region of a current tooth. Using input data that has already been described, the process computes the difference between the desired end position and the achieved end position of the current tooth (462). Using the intersection of the tooth center line with the level of the gum tissue as the point of reference, the process computes the complement of the difference in all six degrees of freedom of motion, namely three degrees of translation and three degrees of rotation (step 464). Next, the model tooth is displaced from its desired end position by the amounts of the complement differences (step 466), which is illustrated in FIG. 9B.

Figure 9D:
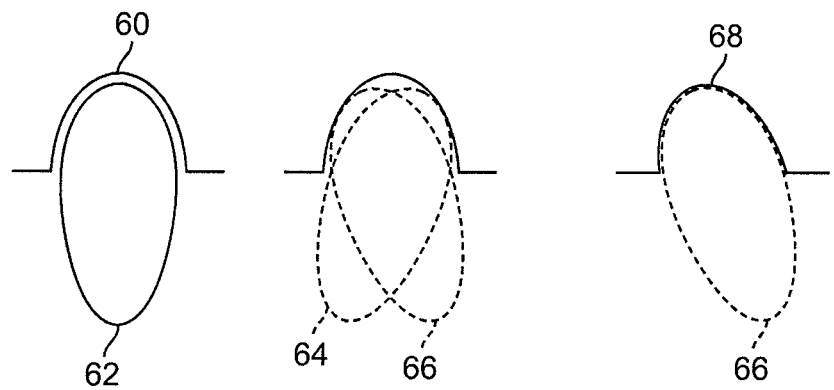
FIG. 9D is a schematic illustrating the operation of the subprocess of FIG. 5B, according to an embodiment of the present invention.

FIG. 9D shows a planar view of an illustrative model aligner 60 over an illustrative model tooth 62. The tooth is in its desired end position and the aligner shape is defined by the tooth in this end position. The actual motion of the tooth calculated by the finite element analysis is illustrated as placing the tooth in position 64 rather than in the desired position 62. A complement of the computed end position is illustrated as position 66. The next step of process 460 (FIG. 9B) defines the aligner in the region of the current tooth in this iteration of the process by the position of the displaced model tooth (step 468) calculated in the preceding step (466). This computed aligner configuration in the region of the current tooth is illustrated in FIG. 9D as shape 68 which is defined by the repositioned model tooth in position 66.

A further step in process 460, which can also be implemented as a rule 452 (FIG. 9A), is shown in FIG. 9C. To move the current tooth in the direction of its central axis, the size of the model tooth defining that region of the aligner, or the amount of room allowed in the aligner for the tooth, is made smaller in the area away from which the process has decided to move the tooth (step 465).

Figure 10:
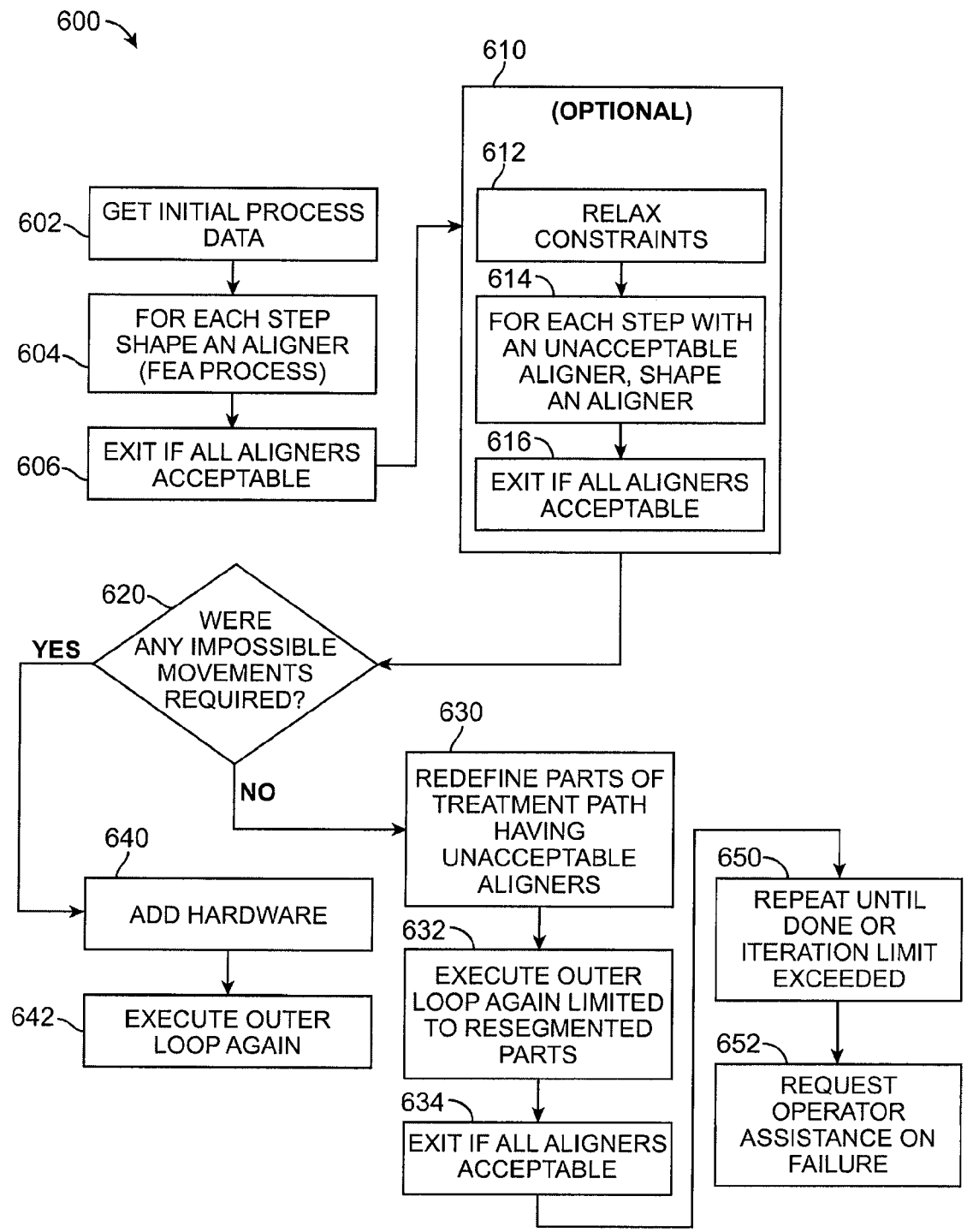
FIG. 10 is a flowchart of a process for computing shapes for sets of aligners, according to an embodiment of the present invention.

As shown in FIG. 10, the process 200 (FIG. 6B) of computing the shape for an aligner for a step in a treatment path is one step in a process 600 of computing the shapes of a series of aligners. This process 600 begins with an initialization step 602 in which initial data, control and constraint values are obtained.

When an aligner configuration has been found for each step or segment of the treatment path (step 604), the process 600 determines whether all of the aligners are acceptable (step 606). If they are, the process is complete. Otherwise, the process optionally undertakes a set of steps 610 in an attempt to calculate a set of acceptable aligners. First, one or more of the constraints on the aligners is relaxed (step 612). Then, for each path segment with an unacceptable aligner, the process 200 (FIG. 6B) of shaping an aligner is performed with the new constraints (step 614). If all the aligners are now acceptable, the process 600 exits (step 616).

Aligners may be unacceptable for a variety of reasons, some of which are handled by the process. For example, if any impossible movements were required (decision step 620), that is, if the shape calculation process 200 (FIG. 6B) was required to effect a motion for which no rule or adjustment was available, the process 600 proceeds to execute a module that calculates the configuration of a hardware attachment to the subject tooth to which forces can be applied to effect the required motion (step 640). Because adding hardware can have an effect that is more than local, when hardware is added to the model, the outer loop of the process 600 is executed again (step 642).

If no impossible movements were required ("no" branch from step 620), the process transfers control to a path definition process (such as step 150, FIG. 6A) to redefine those parts of the treatment path having unacceptable aligners (step 630). This step can include both changing the increments of tooth motion, i.e., changing the segmentation, on the treatment path, changing the path followed by one or more teeth in the treatment path, or both. After the treatment path has been redefined, the outer loop of the process is executed again (step 632). The recalculation is advantageously limited to recalculating only those aligners on the redefined portions of the treatment path. If all the aligners are now acceptable, the process exits (step 634). If unacceptable aligners still remain, the process can be repeated until an acceptable set of aligners is found or an iteration limit is exceeded (step 650). At this point, as well as at other points in the processes that are described in this specification, such as at the computation of additional hardware (step 640), the process can interact with a human operator, such as a clinician or technician, to request assistance (step 652). Assistance that an operator provides can include defining or selecting suitable attachments to be attached to a tooth or a bone, defining an added elastic element to provide a needed force for one or more segments of the treatment path, suggesting an alteration to the treatment path, either in the motion path of a tooth or in the segmentation of the treatment path, and approving a deviation from or relaxation of an operative constraint.

As was mentioned above, the process 600 is defined and parameterized by various items of input data (step 602). In one implementation, this initializing and defining data includes the following items: an iteration limit for the outer loop of the overall process; specification of figures of merit that are calculated to determine whether an aligner is good enough (see FIG. 6B, step 270); a specification of the aligner material; a specification of the constraints that the shape or configuration of an aligner must satisfy to be acceptable; a specification of the forces and positioning motions and velocities that are orthodontically acceptable; an initial treatment path, which includes the motion path for each tooth and a segmentation of the treatment path into segments, each segment to be accomplished by one aligner; a specification of the shapes and positions of any anchors installed on the teeth or otherwise; and a specification of a model for the jaw bone and other tissues in or on which the teeth are situated (in the implementation being described, this model consists of a model of a viscous substrate fluid in which the teeth are embedded and which has boundary conditions that essentially define a container for the fluid).

Various tooth root imaging and/or modeling (e.g., statistical root modeling) may be utilized. The teeth movement can be guided in part using a root-based sequencing system. In one embodiment, the movement is constrained by a surface area constraint, while in another embodiment, the movement is constrained by a volume constraint.

Optionally, other features are added to the tooth model data sets to produce desired features in the aligners. For example, it may be desirable to add digital wax patches to define cavities or recesses to maintain a space between the aligner and particular regions of the teeth or jaw. It may also be desirable to add digital wax patches to define corrugated or other structural forms to create regions having particular stiffness or other structural properties. In manufacturing processes that rely on generation of positive models to produce the repositioning appliance, adding a wax patch to the digital model will generate a positive mold that has the same added wax patch geometry. This can be done globally in defining the base shape of the aligners or in the calculation of particular aligner shapes. One feature that can be added is a rim around the gumline, which can be produced by adding a digital model wire at the gumline of the digital model teeth from which the aligner is manufactured. When an aligner is manufactured by pressure fitting polymeric material over a positive physical model of the digital teeth, the wire along the gumlines causes the aligner to have a rim around it providing additional stiffness along the gumline.

In another optional manufacturing technique, two or more sheets of material are pressure fit over the positive tooth model, where one of the sheets is cut along the apex arch of the aligner and the other(s) is overlaid on top. This provides at least a double thickness of aligner material along the vertical walls of the teeth.

The changes that can be made to the design of an aligner are constrained by the manufacturing technique that will be used to produce it. For example, if the aligner will be made by pressure fitting a polymeric sheet over a positive model, the thickness of the aligner is determined by the thickness of the sheet. As a consequence, the system will generally adjust the performance of the aligner by changing the orientation of the model teeth, the sizes of parts of the model teeth, the position and selection of attachments, and the addition or removal of material (e.g., adding virtual wires or creating protrusions (e.g., ridges, dimples, etc.), creating modification (e.g., modifications to compensate for protrusion mediated distortions)) to change the structure of the aligner. The system can optionally adjust the aligner by specifying that one or more of the aligners are to be made of a sheet of a thickness other than the standard one, to provide more or less force to the teeth. On the other hand, if the aligner will be made by a stereo lithography process, the thickness of the aligner can be varied locally, and structural features such as rims, dimples, and corrugations can be added without modifying the digital model of the teeth.

The system can also be used to model the effects of more traditional appliances such as retainers and braces and therefore be used to generate optimal designs and treatment programs for particular patients.

Thus, one or more shaped features or protrusions can be selectively added and included in appliance design and fabrication, with appliance design and fabrication, and incorporation of appliances in a treatment plan as described above. In some instances, however, incorporation of a shaped feature or protrusion into an appliance may result in a subsequent change in the geometry of the appliance at other surfaces of the appliance, e.g., when worn by the patient. Such changes or alterations can result in changes in property or location of contact surfaces between the tooth and the appliance, sometimes in an undesirable manner. As such, changes or distortions can be modeled or accounted for in appliance design. For example, changes, distortions and the like can be analyzed or determined computationally in terms of probability of occurrence, as well as whether such changes/distortions would be beneficial or detrimental to the desired loading and tooth movement. Methods can be included to determine the effect of these geometric changes and compensate for them by identifying new surfaces or shapes, and loadings to accomplish the desired movement. Appliance geometry can therefore be improved in this iterative design process, as the process in turn considers each feature and its effect on the appliance geometry, on surfaces of contact, and on the force system produced in the designing of an appliance.

Figures 11A, 11B:
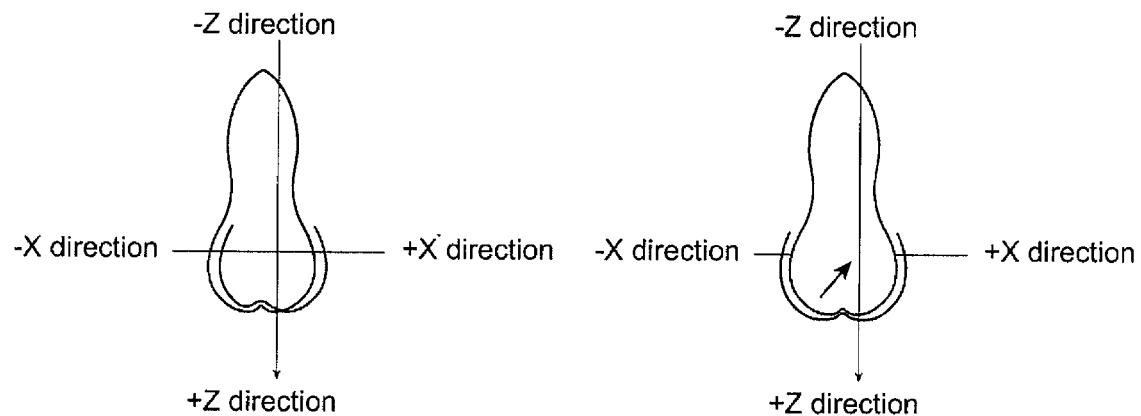
FIGS. 11A-11B illustrate an initial tooth position with a positioned dental appliance, and a resulting undesirable force vector, respectively, according to an embodiment of the present invention.

Modification of an appliance surface to compensate for an effect (e.g., distortion effect) due to incorporation of a protrusion, according to an embodiment of the present invention, is illustrated with reference to FIGS. 11A-11C, and FIG. 12. FIGS. 11A-11B illustrate an initial tooth position with a positioned dental appliance, and a resulting undesirable force vector, respectively. Referring to the Figures, in an example where the tooth as shown is being moved in a facial direction along the x-direction, upon positioning of the dental appliance such as the polymeric shell aligner, over the tooth, the aligner shape geometry is configured to apply a predetermined force upon the tooth to reposition the tooth in accordance with a treatment plan for the particular treatment stage. For example, as shown in FIG. 11B, the dental appliance is configured to fit over the tooth to reposition the tooth in the x-direction as shown, but, rather, results in the application of a predetermined force in the +x/−z direction as shown and illustrated by the arrow. Appliances can include one or more shaped features disposed in a cavity.

Figures 11C, 11D:
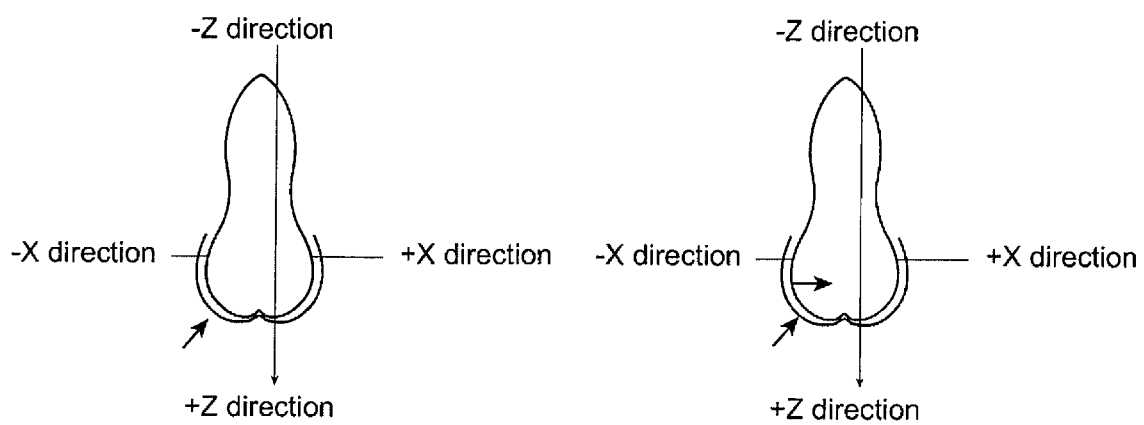
FIGS. 11C-11D illustrate a relief addition to the dental appliance to counteract the undesirable force vector around the tooth, and the resulting desired application of the predetermined force on the tooth by the dental appliance, respectively, according to an embodiment of the present invention.

Accordingly, in one aspect, the aligner shape geometry may be optimized to compensate for the undesirable but resulting force vector so as to counteract its force and further, to apply the intended force in the direction based on the treatment plan for the treatment stage under consideration. One exemplary modification can include addition of a relief component. FIGS. 11C-11D illustrate a relief addition to the dental appliance to counteract the undesirable force vector around the tooth, and the resulting desired application of the predetermined force on the tooth by the dental appliance, respectively. In one aspect, to compensate for the undesirable force (for example, as shown in FIG. 11B by the arrow), a predetermined relief (for example, but not limited to, 0.1 to 0.3 mm) may be provided such that the contact between the aligner and the tooth that resulted in the undesirable force vector is avoided, but still retaining the desired force, for example, along the x-axis as discussed above.

Referring to FIG. 11C, the predetermined relief on the aligner is illustrated by the shown arrow, whereby the engagement between the aligner and the tooth at the location resulting in the undesirable force is removed by modifying the shape of the aligner geometry. In this manner, in one aspect, and as shown in FIG. 11D, the intended and desirable force applied upon the tooth for example, in the x-direction, is achieved by, for example, modifying the aligner shape geometry.

Figure 12:
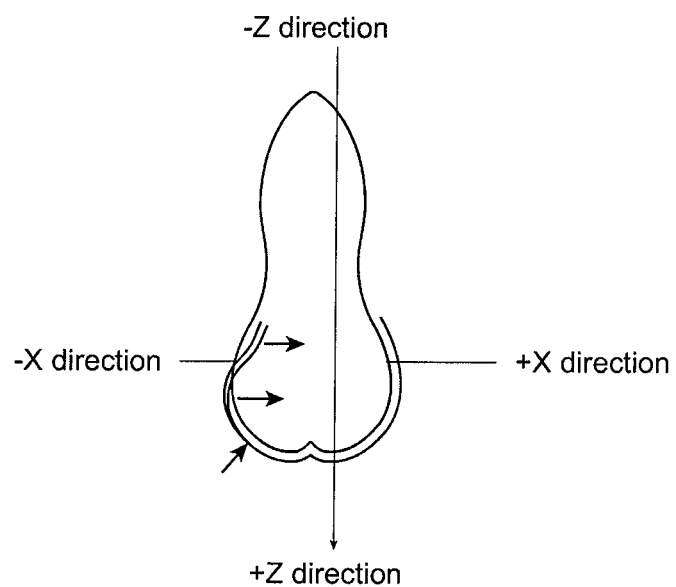
FIG. 12 illustrates a modified dental appliance geometry including an additional shape modification to remove a gap between the dental appliance and the tooth, according to an embodiment of the present invention.

FIG. 12 illustrates a modified dental appliance geometry including an additional shape modification to remove a gap between the dental appliance and the tooth. Referring to FIG. 12, it is to be noted that while the modification of the aligner shape geometry (for example, discussed above in conjunction with FIGS. 11C-11D), results in the desired predetermined force applied upon the tooth as planned for the dental treatment, there may be a gap or pocket that forms between the tooth and the aligner, for example, as shown in FIG. 12, near the gingival area. In one aspect, to account for this gap or pocket generated, the aligner shape geometry may be further modified or optimized, for example, to better adapt in the direction towards the tooth when the aligner is in the active (or stretched) state.

Referring to FIG. 12, the optimization of the aligner shape geometry to address the formed gap or pocket is illustrated by the arrow in one embodiment, in the direction of which, the aligner shape may be modified. Moreover, it should be noted that the optimization of the aligner shape to account for the gap may potentially effect the direction of the applied force on the tooth by the aligner, and thus, may further require additional modification or optimization.

In one aspect, the modification of the dental aligner shape geometry with one or more areas of modification (e.g., relief, etc.), as well as recontouring for looser or tighter adaptation, respectively, to achieve the desired force vector, while avoiding friction and other undesirable force vectors provides improved and customized aligner shape for the treatment of the dental conditions.

In manufacturing of the dental appliances, in one aspect, the stereolithography mold may be adjusted during the build process to take shape of the desired geometry based on, for example, digitally adding and/or subtracting the relief and/or protrusion in predefined or relevant locations of the mold.

In one aspect, based on the force behavior determined from the material properties and the amount of surface area perpendicular to the composite vector resulting from the movement vector for the particular treatment stage, additional surface area may be added to the tooth by employing a shaped feature specifically suited for the desired movement. In this manner, in one aspect, the cross section and/or orientation of the surface area may be determined for a particular tooth, and the shaped feature(s) can be incorporated on one or more teeth to enhance or improve upon the necessary surface area to cooperate or engage with the dental appliance to effect the desired movement vector or the predetermined level of force upon the tooth in the accurate direction for the treatment stage.

In this manner, in one aspect, a dental aligner may be manufactured or simulated using a computer aided design tool or system, where, a representation of the tooth to be moved is first modeled. Thereafter, the aligner that defines the target position of the tooth is modeled with shape geometry properties defined. Thereafter, the force necessary to reposition the tooth from the initial location to the target location is determined or modeled, for example, using FEA modeling, or other suitable computation and/or modeling techniques. In one aspect, it is possible to define the force using a physical model of the teeth connected to force measurement sensors, such that the optimal forces may be determined using the readouts obtained from the physical model, and thus altering the shapes of features (e.g., ridge protrusions, dimpled protrusions, etc.) and aligner configurations based at least in part on the feedback from the physical force gauge.

As a result, a movement vector is defined which establishes the direction of the applied force, as well as the level of force and its properties which are necessary to reposition the tooth from the initial position to the target position. Based on the movement vector, and the modeled aligner shape, the aligner is further modified or reconfigured to factor in the determined movement vector. That is, after having defined the movement vector which identifies the force properties necessary for the tooth repositioning, the dental appliance shape is altered or optimized based on the determined movement vector. Additionally, the appliance shape may be further optimized to counteract the undesirable forces or force components, or appliance distortion (e.g., due to a protrusion) that may result based on the defined movement vector.

Thereafter, the modified or optimized dental appliance may be manufactured through stereolithography or other suitable techniques to attain the desired tooth movement. Further, this process may be repeated for the optimization of dental appliance for each treatment stage of the treatment plan such that the aligner performance and therefore, the treatment plan result is improved.

Furthermore, in yet still another aspect, shaped feature placement may be determined based on the location of the maximum amount of surface area available perpendicular to the desired direction of the tooth movement. Further, if the force on any given tooth in the treatment plan is at or below a predefined level, the feature (e.g., protrusion) may be added to the tooth or appliance to supplement the desired surface area or increase the friction coefficient of the tooth, thereby improving the force profile of the aligner on the tooth.

In one aspect, the data set associated with the teeth, gingiva and/or other oral tissue or structures may be intentionally altered through, for example, addition, partial or total subtraction, uniform or non-uniform scaling, Boolean or non-Boolean algorithm, or geometric operations, or one or more combinations thereof, for the configuration, modeling and/or manufacturing of the dental appliance that may be optimized for the desired or intended treatment goal.

Accordingly, in one aspect, the n+1 or subsequent/target tooth position is first determined. Thereafter, the direction of movement to reach the target tooth position from the initial tooth position is determined. After determining the direction of movement, the amount or magnitude and direction of force and torque to reposition the tooth from the initial position to the target position is determined. Thereafter, profile of the appliance cavity and features/protrusions disposed therein, such as the geometry that would provide the most suitable load vector in the direction of the planned tooth movement is determined, as well as the optimal position of the shaped feature relative to the tooth surface. In this manner, the force/torque generated by the dental appliance is accurately directed in the desired direction, and also is configured with sufficient magnitude to move the tooth into the next planned position.

In one aspect, the direction and the magnitude of the force/torque may be modified or optimized to generate counterbalancing force/torque to eliminate or minimize unwanted tipping torque, to attain root movement, and the like, by adjusting the profile and/or positioning of the shaped features relative to the crown surface, for example. The amount of the feature movement with respect to the tooth crown may also be correlated with the tooth movement to generate a treatment plan based on the movement of the features.

Figure 13:
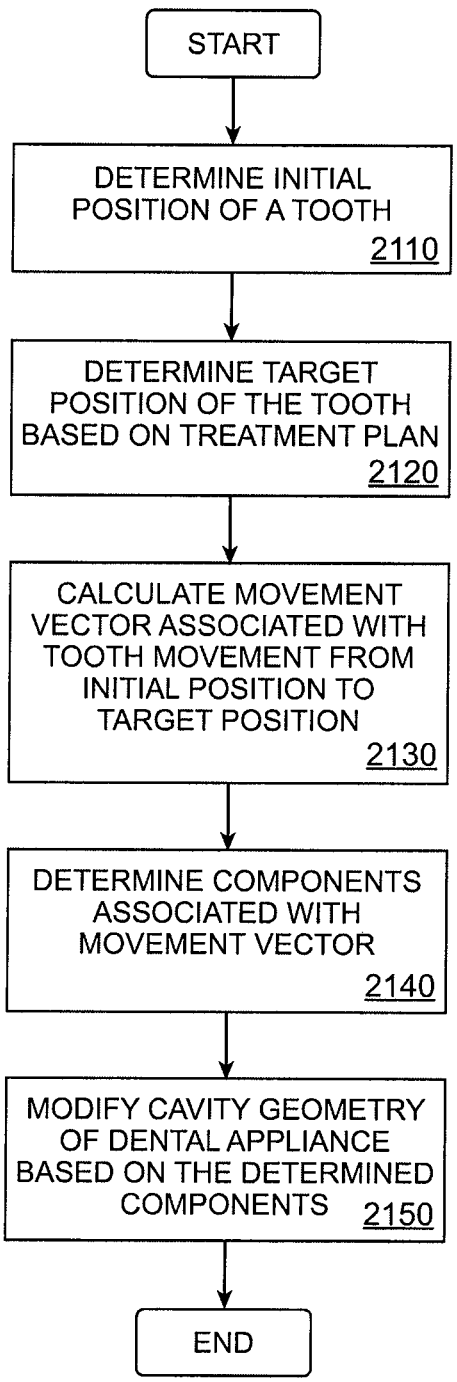
FIG. 13 is a flowchart illustrating the optimized shape geometry of the dental appliance, according to an embodiment of the present invention.
Figure 14:
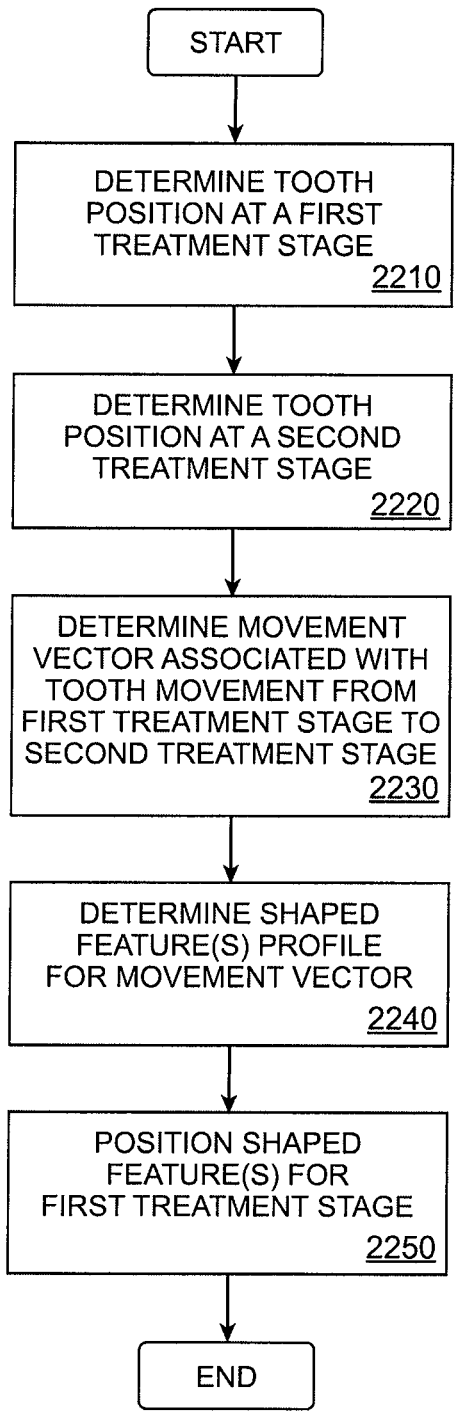
FIG. 14 is a flowchart illustrating a process of shape feature design and positioning, according to an embodiment of the present invention.

FIG. 13 is a flowchart illustrating the optimized shape geometry of the dental appliance. Referring to FIG. 13, at step 2110, the initial position of the tooth is determined. Thereafter, at step 2120, the target position of the tooth based on the treatment plan is determined. In one aspect, the target position may include the next or n+1 treatment stage tooth position. Referring back to FIG. 13, after determining the target position of the tooth based on the treatment plan, a movement vector associated with the tooth movement from the initial position to the target position is calculated or determined at step 2130. That is, a force profile or attributes is determined which includes, for example, the magnitude of the force and the direction of the force, for example, that is associated with the tooth movement from the initial position to the target position.

Referring again to FIG. 13, after determining the movement vector associated with the tooth movement from the initial position to the target position, at step 2140, the components associated with the movement vector are determined. For example, as discussed above, the force magnitude associated with the movement vector to reposition the tooth from the initial position to the target position is determined. Additionally, the force direction for the tooth movement, as well as counter forces for addressing unwanted or unintended forces are determined. Thereafter, based on the determined components associated with the movement vector which is associated with the tooth movement from the initial position to the target position, the cavity geometry of the dental appliance such as the aligner is modified.

FIG. 22 is a flowchart illustrating the shaped feature(s) (e.g., ridges, dimples, etc.) profile determination and positioning. Referring to FIG. 22, at step 2210 the tooth position at a first treatment stage is determined. At step 2220 the tooth position at the second or n+1 treatment stage is determined. Thereafter, the movement vector associated with the tooth movement from the first treatment stage to the second treatment stage is determined at step 2230. After determining the movement vector associated with the tooth movement, one or more shaped feature(s) profile associated with the movement vector is determined at step 2240. Thereafter, at step 2250, the one or more shaped features are positioned, e.g., in the appliance (tooth receiving cavity), for contact with the corresponding tooth during the first treatment stage. The shaped feature profile and positioning are selected to achieve the desired tooth movement.

In this manner, in one embodiment, the force/torque from the dental appliance is accurately applied to the tooth to reposition the tooth from the initial position to the target or second treatment stage position.

The present invention can make use of various computer implemented embodiments of the methods described herein. For example, a computer implemented method in one embodiment includes establishing an initial position of a tooth, determining a target position of the tooth in a treatment plan, calculating a movement vector associated with the tooth movement from the initial position to the target position, determining a plurality of components corresponding to the movement vector, and determining a corresponding one or more positions/profiles of a respective one or more shaped features. The shaped features may be configured to apply a predetermined force on the dental appliance substantially at the surface plane of the tooth.

An apparatus for modeling a dental appliance in another embodiment includes a data storage unit, and a processing unit coupled to the data storage unit and configured to determine an initial position of a tooth, determine a target position of the tooth in a treatment plan, calculate a movement vector associated with the tooth movement from the initial position to the target position, determine a plurality of components corresponding to the movement vector, and determine a profile and/or positioning of corresponding one or more shaped features.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An orthodontic appliance configured for repositioning a patient's teeth, comprising:
a shell appliance having teeth receiving cavities shaped to apply a resiliently repositioning force when the appliance is worn by the patient so as to move the patient's teeth from a current arrangement toward a target arrangement, the shell comprising a ridge-shaped protrusion having a generally semi-circular cross-sectional shape protruding into a repositioning cavity and configured to apply a repositioning force to a patient's tooth corresponding to a selected tooth movement, the ridge-shaped protrusion having a length and a width that differ relative to each other, the length being greater than the width so that the repositioning force is applied along a length of the patient's tooth.

2. The appliance of claim 1, wherein the cavity comprises only a single protrusion.

3. The appliance of claim 1, wherein the cavity comprises a plurality of protrusions.

4. The appliance of claim 3, wherein the plurality of protrusions are shaped such that each of the protrusions is brought into contact with the received patient's tooth when the appliance is initially positioned on the teeth.

5. The appliance of claim 1, wherein the cavity comprises two protrusions positioned to contact substantially opposing sides of a received tooth as the appliance is initially positioned on the tooth.

6. The appliance of claim 5, wherein the two protrusions are selected to reduce a tipping movement of the tooth during repositioning.

7. The appliance of claim 1, wherein the selected tooth movement comprises a buccal translation, lingual translation, mesial translation, distal translation, extrusion, or intrusion.

8. The appliance of claim 1, wherein the selected tooth movement comprises a first, second, or third order root movement.

9. A system configured for repositioning a patient's teeth according to an orthodontic treatment plan, the system comprising:
a plurality of appliances shaped to receive and resiliently reposition teeth through a plurality of planned successive tooth arrangements so as to move the patients teeth along a treatment path from an initial position toward a final position, the appliances having teeth receiving cavities and wherein the cavities of successive appliances have different geometries shaped to receive and reposition teeth from a first position to a successive position, at least one appliance of the plurality comprising a cavity having a ridge-shaped protrusion shaped and positioned in the cavity to apply a repositioning force to a patient's tooth corresponding to a selected tooth movement, the ridge-shaped protrusion having a generally semi-circular cross-sectional shape and a substantially elongate shape, or a length and a width that differ relative to each other, the length being greater than the width so that the repositioning force is applied along a length of the patient's tooth.

10. The system of claim 9, wherein the cavity comprises only a single protrusion.

11. The system of claim 10, wherein the single protrusion is positioned on a buccal side or a lingual side of the cavity.

12. The system of claim 9, wherein the cavity comprises a plurality of protrusions comprising at least two protrusions shaped and positioned in the cavity such that each of the at least two protrusions is brought into contact with the received patient's tooth when the at least one appliance is initially worn by the patient.

13. The system of claim 12, wherein the at least two protrusions are positioned to contact substantially opposing sides of the received tooth.

14. The system of claim 12, wherein the at least two protrusions comprise a first protrusion positioned on a buccal side of the cavity and a second protrusion positioned on a lingual side of the cavity.

15. The system of claim 14, wherein the first protrusion and second protrusion are positioned so as to apply a lingual or buccal translational force to the received tooth.

16. The system of claim 12, the at least two protrusions comprising a first protrusion positioned at a distal interproximal area of the cavity and a second protrusion positioned at a mesial interproximal area.

17. The system of claim 16, wherein the first protrusion and second protrusion are positioned so as to apply a mesial or distal translational force to the received tooth.

18. The system of claim 12, wherein the at least two protrusions are positioned gingivally so as to apply an extrusion force to the received tooth.

19. The system of claim 12, wherein the at least two protrusions are positioned occlusally so as to apply an intrusion force to the received tooth.

20. The system of claim 9, wherein the selected tooth movement comprises a first, second, or third order root movement.

21. The system of claim 9, wherein the plurality of appliances comprise a first appliance to reposition teeth from an initial tooth arrangement to a first intermediate arrangement; at least one intermediate appliance to progressively reposition teeth from the first intermediate arrangement to successive intermediate arrangements; and a final appliance to progressively reposition teeth from a last intermediate arrangement toward a final arrangement.

22. The system of claim 9, wherein the planned successive arrangements are based on models of the patient's teeth generated prior to starting the orthodontic treatment plan.

* * * * *